United States Patent
Sarma et al.

(10) Patent No.: US 9,737,230 B2
(45) Date of Patent: Aug. 22, 2017

(54) SEIZURE DETECTION DEVICE AND SYSTEMS

(75) Inventors: Sridevi V. Sarma, McLean, VA (US); Sabato Santaniello, Baltimore, MD (US); Samuel P. Burns, Philadelphia, PA (US); Munther Dahleh, Cambridge, MA (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 890 days.

(21) Appl. No.: 13/977,477

(22) PCT Filed: Jan. 6, 2012

(86) PCT No.: PCT/US2012/020525
§ 371 (c)(1),
(2), (4) Date: Jun. 28, 2013

(87) PCT Pub. No.: WO2012/094621
PCT Pub. Date: Jul. 12, 2012

(65) Prior Publication Data
US 2013/0274625 A1    Oct. 17, 2013

Related U.S. Application Data

(60) Provisional application No. 61/430,270, filed on Jan. 6, 2011, provisional application No. 61/508,392, filed on Jul. 15, 2011.

(51) Int. Cl.
*A61B 5/04*    (2006.01)
*A61B 5/0476*    (2006.01)
(Continued)

(52) U.S. Cl.
CPC ........... *A61B 5/0476* (2013.01); *A61B 5/048* (2013.01); *A61B 5/0482* (2013.01);
(Continued)

(58) Field of Classification Search
None
See application file for complete search history.

(56) References Cited

U.S. PATENT DOCUMENTS 6,016,449 A * 1/2000 Fischell ............... A61B 5/0476
607/45
6,304,775 B1 * 10/2001 Iasemidis ............. A61B 5/0476
600/544

(Continued)

OTHER PUBLICATIONS

Aarabi et al., (2009) A fuzzy rule-based system for epileptic seizure detection in intracranial EEG. *Clin Neurophysiol*. 120:1648-1657.
(Continued)

*Primary Examiner* — Etsub Berhanu
(74) *Attorney, Agent, or Firm* — Venable LLP; Henry J. Daley

(57) ABSTRACT

A neurostimulation device includes a plurality of electrodes adapted to be electrically connected to a subject to receive multichannel electrical signals from the subject's brain, a multichannel seizure detection unit electrically connected to the plurality of electrical leads to receive the multichannel electrical signals, and a neurostimulation unit in communication with the multichannel seizure detection unit. The plurality of electrodes are at least three electrodes such that the multichannel electrical signals are at least three channels of electrical signals, and the multichannel seizure detection unit detects a presence of a seizure based on multichannel statistics from the multichannel electrical signals including higher order combinations than two-channel combinations.

22 Claims, 8 Drawing Sheets

(51) Int. Cl.
　　　A61B 5/048　　(2006.01)
　　　A61B 5/00　　(2006.01)
　　　A61N 1/36　　(2006.01)
　　　A61B 5/0482　(2006.01)
(52) U.S. Cl.
　　　CPC ........ A61B 5/4094 (2013.01); A61N 1/36064 (2013.01); A61N 1/36135 (2013.01)

(56) References Cited

U.S. PATENT DOCUMENTS

| | | | | |
|---|---|---|---|---|
| 2004/0122335 | A1* | 6/2004 | Sackellares | A61B 5/04008 600/544 |
| 2004/0230105 | A1* | 11/2004 | Geva | A61B 5/04012 600/301 |
| 2006/0149160 | A1* | 7/2006 | Kofol | A61B 5/0476 600/544 |
| 2009/0062696 | A1* | 3/2009 | Nathan | A61B 5/1107 600/595 |
| 2011/0218950 | A1* | 9/2011 | Mirowski | A61B 5/0476 706/12 |

OTHER PUBLICATIONS

Abibullaev et al., (2010) Seizure detection in temporal lobe epileptic EEGs using the best basis wavelet functions. *J Med Syst.* 34:755-765.
Akaike H. (1974) A new look at the statistical model identification. *IEEE Trans Aut Control.* 19:716-723.
Alarcon et al., (1997) Origin and propagation of interictal discharges in the acute electrocorticogram Implications for pathophysiology and surgical treatment of temporal lobe epilepsy. Brain 120:2259-2282.
Alkan et al., (2005) Automatic seizure detection in EEG using logistic regression and artificial neural network. *J Neurosci Methods* 148:167-176.
Anderson et al., (2008) Implantation of a responsive neurostimulator device in patients with refractory epilepsy. *Neurosurg Focus.* 25:E12.
Andrzejak et al., G, Chicharro D, Lehnertz K, Mormann F (2011) Using bivariate signal analysis to characterize the epileptic focus: The benefit of surrogates. Phys. Rev. E 83:046203.
Austin et al., Behavior problems in children before first recognized seizures. Pediatrics, 2001, 107(1):115-122.
Baier et al., (2007) Characterizing correlation changes of complex pattern transitions: The case of epileptic activity. *Phys. Let. A,* 363:290296.
Ben-Jacob et al., (2007) Detecting and localizing the foci in human epileptic seizures. Chaos 17:043113.
Ben-Jacob et al., (2007b) Mapping and assessment of epileptogenic foci using frequency-entropy templates. Phys. Rev. E 76:051903.
Bernhardt et al., (2011) Graph-theoretical analysis reveals disrupted small-world organization of cortical thickness correlation networks in temporal lobe epilepsy. Cereb Cortex 21:2147-2157.
Bertsekas (2005) Dynamic Programming and Optimal Control. Belmont, MA: Athena Scientific.
Bettus (2008) Enhanced EEG functional connectivity in mesial temporal lobe epilepsy. Epilepsy Res. 81:58-68.
Bourgeois et al., Intelligence in epilepsy: A prospective study in children. Annals of Neurology, 1983, 14: 438-444.
Brown et al., (2003) Likelihood methods for neural data analysis. In: Computational neuroscience: a comprehensive approach (J. Feng, ed), pp. 253-286. London, UK: CRC.
Bullmore et al., (2009) Complex brain networks: graph theoretical analysis of structural and functional systems. Nat Rev. Neurosci. 10:186-198.
Chan et al., (2008) Automated seizure onset detection for accurate onset time determination in intracranial EEG. Clin Neurophysiol. 119:2687-2696.

Cockerell et al., Mortality from epilepsy: results from a prospective population-based study. Lancet. Oct. 1, 1994;344(8927):918-21.
Coleman et al., (2010) A computationally efficient method for nonparametric modeling neural spiking activity with point processes. Neural Comp. 22:2002-2030.
Cover et al., (2006) Elements of Information Theory. 2nd edition, WileyInterscience, New York, NY.
de Boer et al., (2008) The global burden and stigma of epilepsy. *Epilepsy Behav.* 12:540-546.
Elger et al., (2008) Modern management of epilepsy: a practical approach. *Epilepsy Behav.* 12:501-539.
Engel J (1994) Epilepsy surgery. *Curr Opin Neurol.* 7:140-147.
Esteller et al., (2005) Continuous energy variation during the seizure cycle: towards an on-line accumulated energy. *Clin Neurophysiol.* 116:517-526.
Fisher et al., (2010) Electrical stimulation of the anterior nucleus of thalamus for treatment of refractory epilepsy. Epilepsia 51:899-908.
Fisher et al., (2005) Epileptic seizures and epilepsy: definitions proposed by the international league against epilepsy (ILAE) and the international bureau for epilepsy (IBE). *Epilepsia* 46:470-472.
Fountas et al., (2005) Implantation of a closed-loop stimulation in the management of medically refractory focal epilepsy: a technical note, Stereotact Funct Neurosurg. 83:153-158.
Franaszczuk et al., (1994) Analysis of mesial temporal seizure onset and propagation using the directed transfer function method. Electroenceph. Clin. Neurophysiol. 91:413-427.
Franaszczuk et al., (1998) Application of the directed transfer function method to mesial and lateral onset temporal lobe seizures. Brain Topogr. 11(1):1321.
Gardner et al., (2007) Human and automated detection of high-frequency oscillations in clinical intracranial EEG recordings. Clin Neurophysiol. 118:1134-1143.
Ghosh-Dastidar et al., (2007) Mixed-band wavelet-chaos-neural network methodology for epilepsy and epileptic seizure detection. IEEE Trans Biomed Eng. 54:1545-1551.
Ghosh-Dastidar et al., (2008) Principal component analysis-enhanced cosine radial basis function neural network for robust epilepsy and seizure detection. IEEE Trans Biomed Eng. 55:512-518.
Goldberger et al., (2000) PhysioBank, PhysioToolkit, and PhysioNet: Components of a new research resource for complex physiologic signals. Circulation 101:e215-e220.
Gotman J (1983) Measurements of small time differences between EEG channels: method and application to epileptic seizure propagation. Electroenceph. Neurophysiol., 56:501-514.
Gotman et al., (1976) Automatic recognition and quantification of interictal epileptic activity in the human scalp EEG. Electroenceph. Clin. Neurophysiol. 41:513-529.
Gotman J. (1982) Automatic recognition of epileptic seizures in the EEG. Electroenceph. Clin. Neurophysiol. 54:530-540.
Grewal et al., (2005) An automatic warning system for epileptic seizures recorded on intracerebral EEGs. Clin. Neurophysiol. 116:2460-2472.
Guo et al., (2010) Automatic epileptic seizure detection in EEGs based on line length feature and artificial neural networks. J. Neurosci. Methods 191:101-109.
Guo et al., (2010) Epileptic seizure detection using multiwavelet transform based approximate entropy and artificial neural networks. J Neurosci Methods 193:156-163.
Haas et al., (2007) Strategies for adapting automated seizure detection algorithms. Med Eng Phys. 29:895-909.
Hoare P. The development of psychiatric disturbance among school children with epilepsy. Dev Med Child Neurol 1984, 26: 23-4.
Iasemidis et al., (2004) Dynamical resetting of the human brain at epileptic seizures: application of nonlinear dynamics and global optimization techniques. *IEEE Trans Biomed Eng.* 51:493-506.
Jerger et al., (2001) Early seizure detection. *J. Clin. Neurophysiol.* 18:259-268.
Jiruska et al., (2010) Effects of direct brain stimulation depend on seizure dynamics. *Epilepsia* 51:S93-S97.
Jobst et al., (2010) Brain stimulation for the treatment of epilepsy. Epilepsia 51:S88-S92.

(56) References Cited

OTHER PUBLICATIONS

Jung et al., (1999) Neocortical temporal lobe epilepsy: intracranial EEG features and surgical outcome. J. Clin. Neurophysiol., 16(5):419428.
Kanemoto et al., (2010) Violence and postictal psychosis: a comparison of postictal psychosis, inter-ictal psychosis, and postictal confusion. Epilepsy Behav. 19:162-166.
Khan et al., (2003) Wavelet based automatic seizure detection in intracerebral electroencephalogram. 1 Clin Neurophysiol. 114:898-908.
Kramer et al., (2010) Coalescence and fragmentation of cortical networks during focal seizures. J. Neurosci. 30(30):10076-10085.
Kramer et al., (2008) Emergent network topology at seizure onset in humans. Epilepsy Res. 79:173-186.
Lai et al., (2004) Controlled test for predictive power of Lyapunov exponents: Their inability to predict epileptic seizures. Chaos, 14(3):630642.
Lee et al., (2007) Comparison of seizure detection algorithms in continuously monitored pediatric patients. J Clin Neurophysiol 24:137-146.
Lee et al., (2005) Surgical outcome and prognostic factors of cryptogenic neocortical epilepsy. Ann Neurol. 58:525-532.
Leonardi et al., (2002) The global burden of epilepsy. Epilepsia 43:S21-S25.
Lhatoo et al., Cause-specific mortality in epilepsy. Epilepsia. 2005;46 Suppl 11:36-9.
Lindsten et al., Mortality risk in an adult cohort with a newly diagnosed unprovoked epileptic seizure: a population-based study. Epilepsia. Nov. 2000;41(11):1469-73.
Liu et al., (2008) Quantitative complexity analysis in multi-channel intracranial EEG recordings from epilepsy brains. J Comb Optim. 15:276-286.
Loiseau et al., Short-term mortality after a first epileptic seizure: a population-based study. Epilepsia. Oct. 1999;40(10):1388-92.
Luders et al., (1992) Conceptual considerations. In Epilepsy Surgery. Raven Press, New York pp. 51-62.
Matsuoka et al., (1993) Seizure localization using subdural grid electrodes. Epilepsia, 34(6):8.
Meier et al., (2008) Detecting epileptic seizures in long-term human EEG: a new approach to automatic online and real-time detection and classification of polymorphic seizure patterns. J Clin Neurophysiol. 25:119-131.
Minasyan et al., (2010) Patient-specific early seizure detection from scalp electroencephalogram. J Clin Neurophysiol. 27:163178.
Morrell (2008) Long-tei safety and efficacy of the RNSTM system in adults with medically intractable partial onset seizures. Proc. American Epilepsy Society Annual Meeting. Abstract No. 8536. www. aesnet. org.
Morrell (2006) Brain stimulation for epilepsy: Can scheduled or responsive neurostimulation stop seizures? *Curr Opin Neurol.* 19:164-168.
Morrell (2011) On behalf of the RNS System in Epilepsy Study Group. Responsive cortical stimulation for the treatment of medically intractable partial epilepsy. *Neurol*; 77:1295-1304.
Muller et al., (2005) Detection and characterization of changes of the correlation structure in multivariate time series. Phys. Rev. E 71:046116.
Nashef et al., (1995) Sudden death in epilepsy: a study of incidence in a young cohort with epilepsy and learning difficulty. Epilepsia 36:1187-1194.
Nilsson et al., (1997) Cause-specific mortality in epilepsy: a cohort study of more than 9,000 patients once hospitalized for epilepsy. Epilepsia 38: 1062-1068.
Olafsson et al., Long-term survival of people with unprovoked seizures: a population-based study. Epilepsia. Jan. 1998;39(1):89-92.
Osorio et al., (2002) Performance reassessment of a real-time seizure-detection algorithm on long ECoG series. Epilepsia 43:1522-1535.
Osorio et al., (1998) Real-time automated detection and quantitative analysis of seizures and short-term prediction of clinical onset. Epilepsia 39:615-627.
Osorio et al., (2009) Real-time detection, quantification, warning, and control of epileptic seizures: the foundations for a scientific epileptology. Epilepsy Behav. 16:391-396.
Osterhage et al., (2008) Detecting directional coupling in the human epileptic brain: Limitations and potential pitfalls. Phys Rev. E, 77:011914.
Palus et al., (2001) Synchronization as adjustment of information rates: Detection from bivariate time series. Phys Rev. E 63:046211.
Perucca et al., (2005) Overtreatment in epilepsy. How it occurs and how it can be avoided. CNS Drugs 19:897-908.
Ponten (2007) Small-world networks and epilepsy: Graph theoretical analysis of intracerebrally recorded mesial temporal lobe seizures. Clin. Neurophys. 118:918-927.
Ponten (2009) Indications for network regularization during absence seizures: Weighted and unweighted graph theoretical analyses. Exp. Neurology 217:197-204.
Risinger et al., (1989) Ictal localization of temporal seizures with scalp-sphenoidal recordings. Neurology 39:1288-1293.
Rummel et al., (2011) Uniform approach to linear and nonlinear interrelation patterns in multivariate time series. Phys. Rev. E 83:066215.
Rummel et al., (2007) The influence of static correlations on multivariate correlation analysis of the EEG. J. Neurosci. Meth. 166:138-157.
Rummel et al., (2010) Analyzing spatiotemporal patterns of genuine cross-correlations. J. Neurosci. Meth. 191:94-100.
Saab et al., (2005) A system to detect the onset of epileptic seizures in scalp EEG. Clin Neurophysiol. 116:427-442.
Sabesan et al., (2009) Information flow and application to epileptogenic focus localization from intracranial EEG. IEEE Trans. Neural Sys. Rehab. Eng. 17(3):244-253.
Sackellares et al., (2006) Predictability analysis for an automated seizure prediction algorithm. J Clin Neurophysiol, 23: 509-520.
Sander JW (2003) The epidemiology of epilepsy revisited. Curr Opin Neural. 16:165-170.
Sarma et al., (2010) Using point process models to compare neuronal activity in sub-thalamic nucleus of Parkinson's patients and a healthy primate. IEEE Trans Biomed Eng. 57:1297-1305.
Sarma et al., (2011) Quickest detection of state-transition in point processes: application to neuronal activity. Proc. 18th IFAC World Conference. Milan, Italy, Aug. 29-Sep. 2, 2011.
Schevon et al., (2007) Cortical abnormalities in epilepsy revealed by local EEG synchrony. NeuroImage 35:140:148.
Schindler et al., (2008) Evolving functional network properties and synchronizability during human epileptic seizures. Chaos 18:033119.
Schindler et al., (2010) Periictal correlation dynamics of high-frequency (80-200 Hz) intracranial EEG. Epilepsy Res. 89:72-81.
Schindler (2007) Assessing seizure dynamics by analysing the correlation structure of multichannel intracranial EEG. Brain 130:6577.
Schmidt (2009) Drug treatment of epilepsy: options and limitations. Epilepsy Behav. 15:56-65.
Seidenberg et al., Academic achievement of children with epilepsy. Epilepsia 1986, 27: 753-759.
Shiryayev (1963) On optimum methods in quickest detection problems. Theory Probab Appl. 8: 22-46.
Shoeb A (2009) Application of Machine Learning to Epileptic Seizure Onset Detection and Treatment. PhD Thesis, Massachusetts Institute of Technology.
Shoeb et al., (2004) Patient-specific seizure onset detection, Epilepsy Behav. 5:483-498.
Shoeb et al., (2009) Non-invasive computerized system for automatically initiating vagus nerve stimulation following patient-specific detection of seizures or epileptiform discharges. Int J Neural Syst. 19:157-172.
Srinivasan et al., (2007) Approximate entropy-based epileptic EEG detection using artificial neural networks. IEEE Trans Inf Technol Biomed. 11:288-295.

(56) References Cited

OTHER PUBLICATIONS

Staniek et al., (2008) Symbolic transfer entropy. Phys Rev. Let. 100:158101.

Tellez-Zenteno et al., Sudden unexpected death in epilepsy: evidence-based analysis of incidence and risk factors. Epilepsy Res. Jun. 2005;65(12):101-15.

Temko et al., (2011) EEG-based neonatal seizure detection with Support Vector Machines. Clin Neurophysiol. 122:464-473.

Theodore et al., (2006) Epilepsy in North America: a report prepared under the auspices of the global campaign against epilepsy, the International Bureau for Epilepsy, the International League Against Epilepsy, and the World Health Organization. Epilepsia 47:1700-1722.

Tito et al., (2009) Seizure detection: an assessment of time- and frequency-based features in a unified two-dimensional decisional space using nonlinear decision functions J Clin Neurophysiol. 26:381391.

van Putten et al., (2005) Detecting temporal lobe seizures from scalp EEG recordings: a comparison of various features. Clin Neurophysiol. 116:2480-2489.

Warren C P, Hu S, Stead M, Brinkmann B H, Bower M R, Worrell G A (2010) Synchrony in normal and focal epileptic brain: the seizure onset zone is functionally disconnected. J. Neurophysiol. 104:3530-3539.

Wilke et al., (2011) Graph analysis of epileptogenic networks in human partial epilepsy. Epilepsia, 52(1):84-93.

Wilson SB, (2005) A neural network method for automatic and incremental learning applied to patient-dependent seizure detection. Clin Neurophysiol. 116:1785-1795.

Wilson SB. (2006) Algorithm architectures for patient dependent seizure detection. Clin Neurophysiol 117:1204-1216.

Yu AJ. Optimal change-detection and spiking neurons. Neural Information Processing Systems Conference (NIPS) 2006: 1545-1552.

Zaveri et al., (2009) Localization-related epilepsy exhibits significant connectivity away from the seizure-onset area. NeuroReport, 20:891-895.

Santaniello, Sabato et al., "Quickest detection of drug-resistant seizures: An optimal control approach." Epilepsy & Behavior, Dec. 2011, vol. 22, pp. S49-S60.

\* cited by examiner

SEIZURE DETECTION DEVICE AND SYSTEMS

CROSS-REFERENCE OF RELATED APPLICATION

This is a national stage application under 35 U.S.C. §371 of PCT/US2012/20525, filed Jan. 6, 2012, which claims priority to U.S. Provisional Application No. 61/430,270, filed Jan. 6, 2011, and U.S. Provisional Application No. 61/508,392, filed Jul. 15, 2011, the entire contents of which are hereby incorporated by reference.

BACKGROUND

1. Field of Invention

The field of the currently claimed embodiments of this invention relates to seizure detection devices and systems.

2. Discussion of Related Art

Epilepsy has a prevalence of about 1% in children and adults 1-8, and is characterized by chronically recurring seizures without clear precipitants 12. A seizure is a finite-time episode of disturbed cerebral function with abnormal, excessive, and synchronous electrical discharges in large groups of cortical neurons 9. Disturbances may be associated with debilitating phenomena (e.g., convulsions, low responsiveness, etc.) or remain clinically unapparent, have a duration ranging from seconds to minutes 33, and may be followed by post-ictal periods of confusion, psychosis, or sensory impairment which can last up to several hours 14-16. Epilepsy in children is associated with problems including academic achievement, behavioral and emotional adjustment, and social competence 3-5, and contributes to 0.5% of the global economic burden of diseases 12.

Despite a large variety of medications available to treat epilepsy [9]-[13], 25% of children (30% of adults) are drug-resistant. Furthermore, since medications are administered without any knowledge of an impending seizure, overtreatment is frequent and may lead to increased morbidity, psychosocial handicaps and mortality [1] [15][16]. Children are the most at risk for developing long-term morbidity, as poorly controlled seizures can affect long term cognitive development and function. Alternative treatments for drug-resistant patients include surgical resection of the epileptogenic zone [17][24] and neurostimulation [14]-[28]. Surgical resection is widely accepted but is not always possible and its success mostly depends on the correct localization of the epileptic focus [17] and the specific cortical area to be resected [24]. Chronic open- and closed-loop neurostimulation are still under clinical trials for adults, and although the results are encouraging [47][25], their therapeutic effectiveness critically depends on electrode placement, coverage, morphology of seizure, and most importantly seizure onset detection [14].

The accurate detection of seizure onsets from sequential iEEG (intracranial electroencephalography) measurements is fundamental for the development of both responsive neurostimulation and effective patient-warning devices. Several OSD (online seizure detection) algorithms have been proposed thus far [47]-[80] and though they are highly sensitive (large number of true positives), these algorithms generally have low specificity (large number of false positives), which limits their clinical use. NeuroPace Inc. has pioneered the development and testing of a closed-loop device, the RNS™ system, which automatically detects an approaching seizure by monitoring two iEEG channels and responds with high frequency periodic stimulation in drug-resistant epilepsy patients [30]. Despite promising results in small populations of patients after short-term follow ups (less than 2 years) [29][30], a recent long-term (5 years) study [31][32] has indicated that the device reduces the number of seizures by 50% in less than 30% of the patients (reduction computed vs. the baseline pre-treatment condition), which is about as effective as a new medication in patients with drug-resistant partial seizures. Although the detection algorithms can be tuned for seizures in a given patient, these simple algorithms lack specificity with many detections of inter-ictal activity that are not destined to evolve into electrical or clinical seizure activity. Since detections result in activation of closed-loop therapy, stimulations are frequently delivered when no seizure occurs. While no significant side effects of stimulation were observed in the RNS trial, increased stimulation frequency can dramatically reduce battery life (typically to 1-2 years [29]). In other studies, there are reports of possible consequences of repetitive stimulation including depression, memory impairment and confusion [49].

The lack of specificity of current OSD algorithms including the one implemented in the RNS™ system presumably occurs because (i) they compute statistics from 1-2 channels at a time that may not capture network dynamics of the brain, and/or (ii) the detection thresholds are not optimized to maximize OSD performance. By optimally detecting when a seizure occurs, specificity of detection would increase and non-specific closed-loop therapy would decrease.

Automatic online seizure detection (OSD) in intractable epilepsy has generated great interest in the last twenty years and is a fundamental step toward the development of anti-epileptic responsive neurostimulation [14]-[28]. Pioneering works in the late 1970s and 1980s by Gotman et al. [50][51] showed that seizures can be automatically separated from inter-ictal activity, and since then, several approaches to OSD have been proposed by exploiting either scalp or intracortical EEG recordings, single or multi-channel analysis, linear or nonlinear features.

Osorio et al. [52]-[55] used a wavelet-based decomposition of selected iEEG recordings to (i) separate the seizure-related component from the background noise, (ii) track the ratio between these components in the time-frequency domain, and (iii) detect a seizure when such a ratio crosses a fixed threshold for a sufficiently long time. Parameters of the detection method (e.g., threshold, duration of the supra-threshold condition, etc.) can be either fixed [52] or adaptive [53][54]. Fixed threshold-based approaches were also proposed in [56]-[58], where the threshold was applied to linear spectral features of the iEEG recordings.

Gotman et al. [59]-[61]proposed a probabilistic framework for seizure detection using scalp EEG [59][61] and iEEG [60] recordings. For each channel, amplitude and energy measures in multiple frequency bands are computed via wavelet decomposition and the corresponding probability distribution function is estimated. Then, the probability of a seizure is conditioned on the value of such measures and estimated via Bayes' rule. A patient-specific threshold is finally applied on this conditional probability of seizure to decide, for each channel, whether a seizure is likely, and a seizure is detected when that threshold is passed in a sufficient number of channels.

More recently, this paradigm has been implemented using sophisticated classification tools. In particular, iEEG channels have been processed individually to extract multiple univariate or bivariate features in the time, frequency domain or the wavelet [62]-[78] domain. Then, for each channel, the features have been combined into vectors and classified via support vector machines (SVMs) [67][69][72][75], principal components analysis (PCA) [73][74], artificial neural networks (ANNs) [62][64]-[66][70][76]-[78], fuzzy logics [68], or pattern recognition tools [63]. Finally, decisions made for different channels are combined or ranked to ultimately determine whether or not a seizure has occurred. As a variation to this paradigm, [72][79] merged features extracted from different channels into one vector and applied a classification rule on this vector.

In the current paradigm, OSD is solved by (i) computing a statistic from a few iEEG measurements at a time, and (ii) then constructing a threshold or classification rule that, based on this statistic, determines whether or not a seizure has occurred (FIG. 2A). The choice of the threshold is traditionally supervised and depends on the fluctuations of the statistic, the specific patient, or the electrode position, and requires long training sessions to be more accurate. Sophisticated classifiers generate unsupervised criteria that separate the feature space into dominant ictal and non-ictal regions but without penalties for specific performance goals (e.g. minimize false positives). All such thresholds trigger too many false alarms when applied to test data. Consequently, all efforts put towards improving OSD algorithms have been in either identifying better statistics with fancy signal processing and/or in implementing more sophisticated classifiers borrowed from the machine learning community. The fundamental problem with this paradigm is that detection performance is not measurable until after implementation ("algorithm defines performance"). There thus remains a need for improved seizure detection devices and systems.

SUMMARY

A neurostimulation device according to some embodiments of the current invention includes a plurality of electrodes adapted to be electrically connected to a subject to receive multichannel electrical signals from the subject's brain, a multichannel seizure detection unit electrically connected to the plurality of electrical leads to receive the multichannel electrical signals, and a neurostimulation unit in communication with the multichannel seizure detection unit. The plurality of electrodes are at least three electrodes such that the multichannel electrical signals are at least three channels of electrical signals, and the multichannel seizure detection unit detects a presence of a seizure based on multichannel statistics from the multichannel electrical signals including higher order combinations than two-channel combinations.

A multichannel seizure detection system according to some embodiments of the current invention includes a signal interface adapted to receive multichannel electrical signals from the subject's brain, and a data processor configured to receive the multichannel electrical signals and detect a presence of a seizure based on multichannel statistics from the multichannel electrical signals including higher order combinations than two-channel combinations. The multichannel electrical signals are at least three channels of electrical signals.

BRIEF DESCRIPTION OF THE DRAWINGS

Further objectives and advantages will become apparent from a consideration of the description, drawings, and examples.

DETAILED DESCRIPTION

Figure 1:
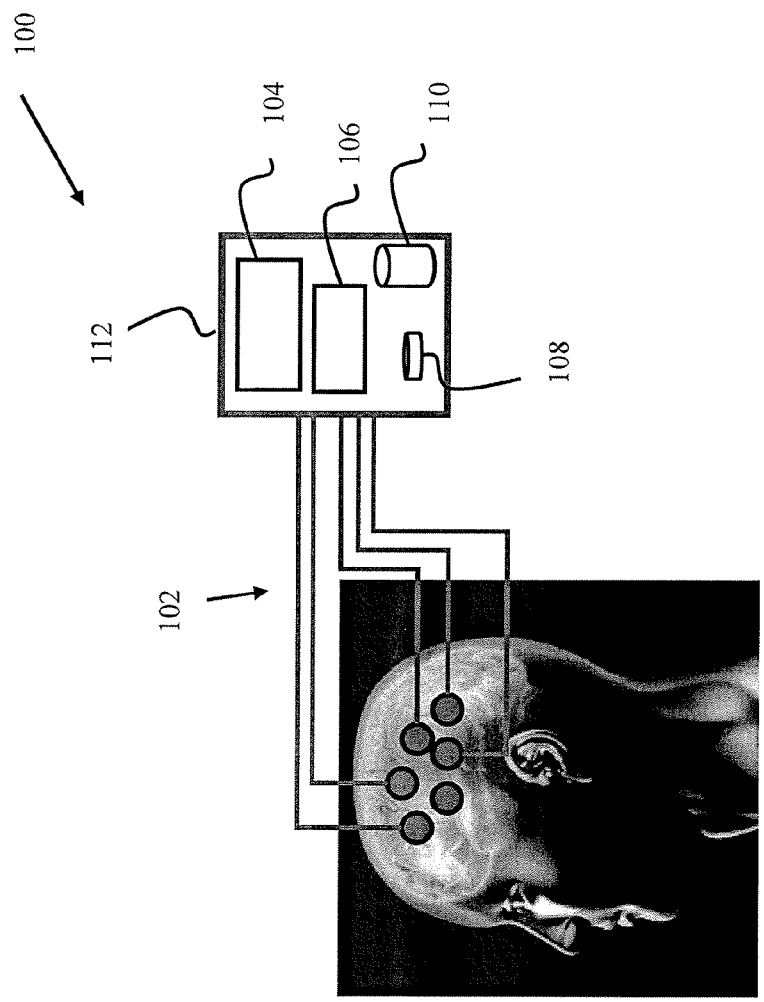
FIG. 1 is a schematic illustration of a neurostimulation device according to an embodiment of the current invention.
Figures 2A, 2B:
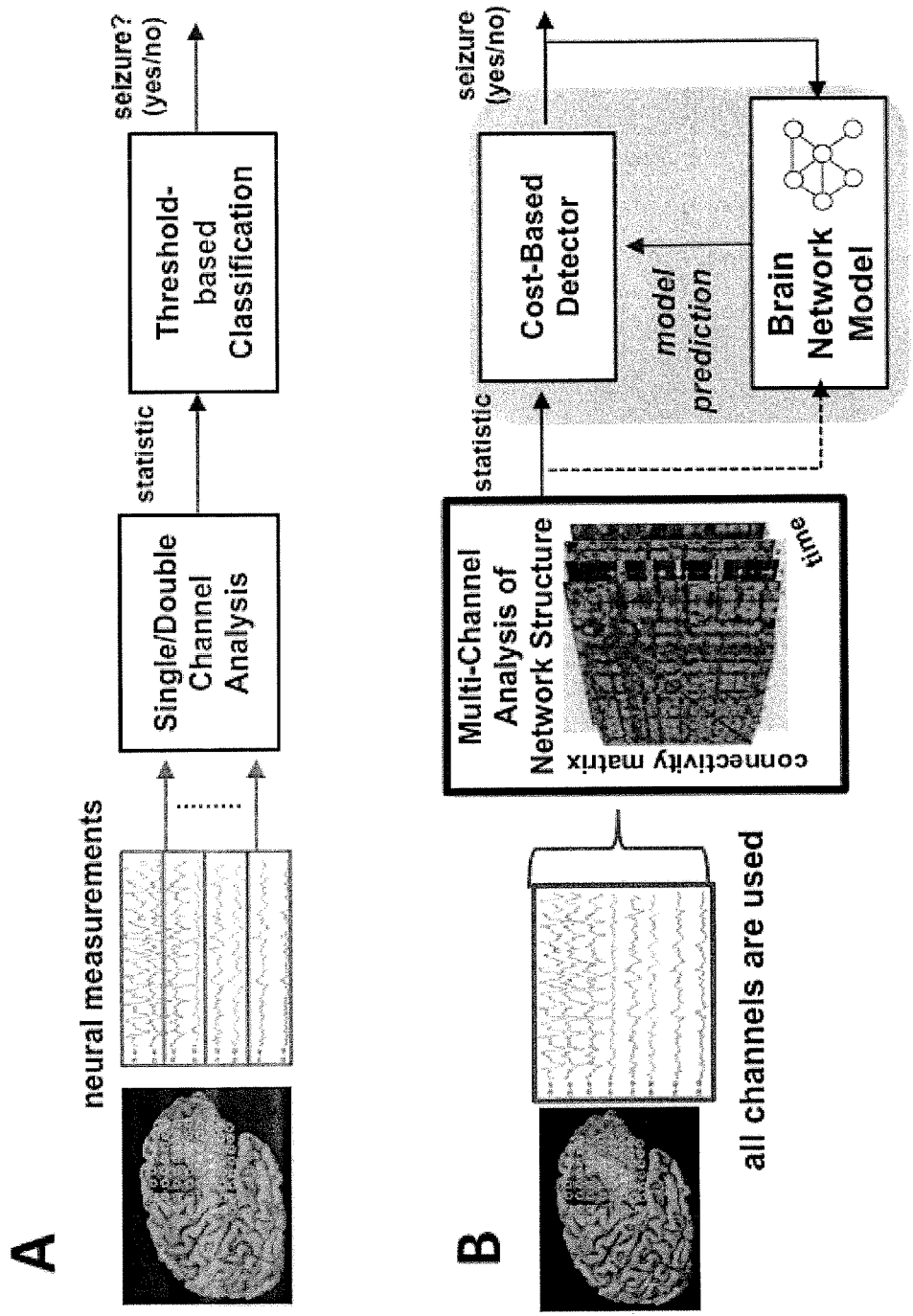
FIGS. 2A and 2B contrast conventional approaches (top) with an embodiment of the current invention (bottom: Multivariate QD approach to OSD).

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The following defines various abbreviations and terms used throughout the description:

iEEG: intracranial EEG is an invasive technique based on recording electroencephalography (EEG) signals directly from the human cortex, as opposed to surface recordings in scalp-EEG. This is achieved either by using subdural grids or strips of electrodes placed directly on the surface of the cortex (also known as Electrocorticography), or using multi-lead depth electrodes.

ECoG: electrocorticography (see iEEG).

OSD: online seizure detection. An algorithm that measures iEEG activity sequentially and estimates the onset times of each seizure.

EMU: epilepsy monitoring unit ictal: ictal refers to a physiologic state or event, for example, a seizure.

QD: quickest detection is a change point detection algorithm that minimizes detection delay and probability of false alarm.

SVD: In linear algebra, the singular value decomposition (SVD) is a factorization of a real or complex matrix, with many useful applications in signal processing and statistics.

HMM: hidden Markov model. A specific model where the states are unobservable but whose outputs are observable/measureable. It is a statistical Markov model in which the system being modeled is assumed to be a Markov process with unobserved (hidden) states. An HMM can be considered as the simplest dynamic Bayesian network. In a regular Markov model, the state is directly visible to the observer, and therefore the state transition probabilities are the only parameters. In a hidden Markov model, the state is not directly visible, but output, dependent on the state, is visible. Each state has a probability distribution over the possible output tokens. Therefore the sequence of tokens generated by an HMM gives some information about the sequence of states. Note that the adjective 'hidden' refers to the state sequence through which the model passes, not to the parameters of the model; even if the model parameters are known exactly, the model is still 'hidden'.

SVM: support vector machine. A support vector machine (SVM) is a concept in computer science for a set of related supervised learning methods that analyze data and recognize patterns, used for classification and regression analysis. The standard SVM takes a set of input data and predicts, for each given input, which of two possible classes comprises the input, making the SVM a non-probabilistic binary linear classifier. Given a set of training examples, each marked as belonging to one of two categories, an SVM training algorithm builds a model that assigns new examples into one category or the other. An SVM model is a representation of the examples as points in space, mapped so that the examples of the separate categories are divided by a clear gap that is as wide as possible. New examples are then mapped into that same space and predicted to belong to a category based on which side of the gap they fall on.

PCA: Principal component analysis (PCA) is a mathematical procedure that uses an orthogonal transformation to convert a set of observations of possibly correlated variables into a set of values of uncorrelated variables called principal components. The number of principal components is less than or equal to the number of original variables. This transformation is defined in such a way that the first principal component has as high a variance as possible (that is, accounts for as much of the variability in the data as possible), and each succeeding component in turn has the highest variance possible under the constraint that it be orthogonal to (uncorrelated with) the preceding components.

ANN: An artificial neural network, usually called neural network (NN), is a mathematical model or computational model that is inspired by the structure and/or functional aspects of biological neural networks. A neural network consists of an interconnected group of artificial neurons, and it processes information using a connectionist approach to computation.

DP: Dynamic Programming: In mathematics and computer science, "dynamic programming" is a method for solving complex problems by breaking them down into simpler subproblems. It is applicable to problems exhibiting the properties of overlapping subproblems which are only slightly smaller and optimal substructure. When applicable, the method takes far less time than naive methods. The key idea behind dynamic programming is quite simple. In general, to solve a given problem, we need to solve different parts of the problem (subproblems), then combine the solutions of the subproblems to reach an overall solution. Often, many of these subproblems are really the same. The dynamic programming approach seeks to solve each subproblem only once, thus reducing the number of computations. This is especially useful when the number of repeating subproblems is exponentially large.

As described in the background section, according to conventional approaches, OSD is solved by (i) computing a statistic from iEEG measurements that captures changes in brain activity at the seizure onset, and (ii) by constructing a threshold or classification rule that, based on this statistic, determines whether or not a seizure has occurred. The choice of the threshold is typically supervised and depends on the fluctuations of the statistic, the specific patient, and/or the electrode position. Such thresholds trigger too many false alarms when applied to test data because the statistic and/or threshold does not separate ictal (seizure) from non-ictal activity well. Furthermore, true positives may be detected with unacceptably long delays. Consequently, all efforts put towards improving OSD algorithms have been in either identifying better statistics with fancy signal processing and/or in implementing more sophisticated classifiers borrowed from the machine learning community. A problem with this paradigm is that detection performance (e.g. number of false positives) is not measurable until after implementation ("algorithm defines performance").

Instead, some embodiments of the current invention take a fresh new approach to OSD. First, we note that classification rules, no matter how fancy, do not account for temporal dependencies and dynamics that exist in neural data. For example, a statistic measured at some time t depends on what values it took on in the past 100-500 ms. Therefore one should model this evolution—it is not what the iEEG activity looks like at any given moment, but how it got there. Predictions from this model should then be used to adapt the threshold rule. For example, if the dynamics appear to be evolving to an ictal state, then the threshold should drop, making it easier to detect a seizure onset. However, the threshold should adapt in an unsupervised and optimal way. Optimality should be defined by maximizing detection performance ("performance defines algorithm!").

To address the raised issues, some embodiments of the current invention provide a novel computational framework for OSD that involves (i) constructing multivariate statistics from all electrodes to distinguish between non-ictal vs. ictal states; (ii) modeling the evolution of these statistics in each state and the state-transition probabilities; and, (iii) developing an optimal model-based strategy to detect transitions to ictal states from sequential neural measurements. This strategy is formulated as the Bayesian "Quickest Detection" (QD) of the seizure onset, and is solved via control optimization tools, and explicitly minimizes both the distance between detected and unequivocal onset times and the probability of false alarm. This is a paradigm shift and (i)-(iii) are described in detail below.

Some embodiments of the current invention may enable more robust detection of seizures for closed-loop intervention. Posthoc review of patient iEEG records (offline seizure confirmation) can also be made more efficient. Overall, the outcomes can lead to more effective treatments, which could potentially avoid fatal accidents thereby saving lives, extending life-expectancy, and improving the administration of anti-seizure drugs.

FIG. 1 is a schematic illustration of a neurostimulation device 100 according to some embodiments of the current invention. The neurostimulation device 100 includes a plurality of electrodes 102 adapted to be electrically connected to a subject to receive multichannel electrical signals from the subject's brain, a multichannel seizure detection unit 104 electrically connected to the plurality of electrical leads 102 to receive the multichannel electrical signals, and a neurostimulation unit 106 in communication with the multichannel seizure detection unit 104. The neurostimulation device 100 can also include other components, such as a power supply 108 and/or data memory or storage components 110. The power supply can include a battery or other electrical power storage devices, for example. The multichannel seizure detection unit 104 and/or the neurostimulation unit 106 can be at least partially implemented on a data processor encoded with software, or could be implemented on hard-wired devices, for example. The electronics of the neurostimulation device 100 can be packaged together in a case 112 in some embodiments. The electrodes 102 can be attached externally or intracranially, depending on the application. Also, in some embodiments, the case 112 can also be implantable such that the neurostimulation device 100 is an implantable device. However, the general concepts of the current invention are not limited to only implantable devices. In other embodiments, the neurostimulation device 100 can be an external device with electrodes attached to the subject's scalp.

The plurality of electrodes 102 are at least three electrodes such that the multichannel electrical signals are at least three channels of electrical signals. However, the broad concepts of the current invention are not limited to only three electrodes. In some embodiments, there can be up to 10, 20, 30, 50 or even more electrodes, depending on the particular application.

The multichannel seizure detection unit 104 detects a presence of a seizure based on multichannel statistics from the multichannel electrical signals including higher order combinations than two-channel combinations. In other words, statistics are not determined for only signals within single channels and correlations between pairs of channels. They are also based on triplets of channels, etc.

In some embodiments of the current invention, multichannel seizure detection unit 104 is configured to model the multichannel electrical signals based on a brain network model. In some embodiments, the brain network model models time-dependent variations of the multichannel statistics. In some embodiments, the brain network model is a Hidden Markov Model. However, the broad concepts of the current invention are not limited to only Hidden Markov Models. In some embodiments, the multichannel seizure detection unit 104 is configured to detect the presence of the seizure based on a time-dependent threshold. In some embodiments, the multichannel seizure detection unit 104 is configured to detect the presence of the seizure based on optimizing a cost function. The cost function can be dependent on a time delay between an actual seizure and a prediction of the seizure, for example. In some embodiments, the cost function can be further dependent on a probability of a false positive detection. In some embodiments, the neurostimulation unit 106 can be configured to provide an electrical stimulation to the subject's brain. Alternatively, or in addition, the neurostimulation unit 106 can be configured to provide a chemical stimulation. Alternatively, or in addition, the neurostimulation unit 106 can be configured to provide other types of stimulation such as feedback and/or signals. The neurostimulation unit 106 can be responsive to output from the multichannel seizure detection unit 104 in some embodiments. For example, the multichannel seizure detection unit 104 can trigger the neurostimulation unit 106. In some embodiments, the multichannel seizure detection unit 104 can be used alone without a neurostimulation unit 106 and/or in conjunction with other devices.

(i) Multivariate Statistics

To identify robust multivariate statistics for seizure detection, multi-site iEEG signals can be processed into generalized non-square connectivity matrices that describe the time-varying spectral dependencies between all the channels over multiple frequency bands. The singular value decomposition (SVD), a tool from matrix theory that highlights dependencies within a matrix, can be used to extract multivariate statistics (e.g., leading singular vector) that capture the dynamics of the brain network in non-ictal and ictal states.

To construct models describing the evolution of multivariate statistics, we note that the network-based statistics evolve over time because of subclinical changes of brain activity that affect iEEG data in time and frequency. To estimate these changes, we can model the evolution of each SVD statistic through a Hidden Markov Model (HMM). The HMMs can be estimated from data for each patient and will characterize (i) neural dynamics in non-ictal and ictal states, and (ii) the probability distribution of the actual transition (T) from any non-ictal to ictal state.

For some applications, for each patient, iEEG recordings can be used to (i) construct a time sequence of connectivity matrices, $\{A(k)\}$, (ii) compute the SVD for each matrix, and (iii) track the leading singular value, $\{\sigma_1(k)\}$, and the corresponding singular vector, $\{u_1(k)\}$ to be used for OSD. These statistics, defined below, may significantly modulate during seizure.

Recent studies have introduced schemes that simultaneously analyze all the available recording channels 86-99106-108. In these schemes, each channel is treated as a node in a graph, and any two nodes are considered connected (i.e., an edge exists between them) if the activity at these sites are dependent. The connectivity (topology) of the graph can then be described by a matrix, which is referred to as the "connectivity" or "adjacency" matrix 109). Statistics computed from this matrix can show if the topology changes significantly from non-ictal to ictal states, and significant changes in these statistics can be used to detect a seizure's onset.

The connectivity matrix, A, can be computed in several ways. In order to capture linear dependencies between all of the recording sites, we can compute connectivity as the cross-power in different frequency bands (theta, alpha etc.) between all available iEEG channels. That is, for each pair of channels (i,j) the corresponding element of the connectivity matrix in the frequency band $F^k$ is $$A_{ij}^{F^k} \triangleq \int_{F_k} P_{ij}(f) df, \quad (1)$$

where $P_{ij}(f)$ is the cross-power spectral density of channels i and j at frequency f 110. The frequency bands will include: $F_1=[4,7]$ Hz (theta band), $F_2=[8,13]$ Hz (alpha band), $F_3=[13,35]$ Hz (beta band), and the final non-square connectivity matrix will be (for these bands)

$$A = [A^{F_1} A^{F_2} A^{F_3}]. \quad (2)$$

One can compute A over a sliding window, which will result in a sequence of matrices $\{A(k)\}$, one per window. Based on data provided later in this section, one can initially use 5 s-long windows with 1 s slide, which will result in a connectivity matrix $A(k)$ at each time second k.

Singular Value Decomposition (SVD)

Measures off of the connectivity matrix (2) can be computed to generate multivariate statistics that significantly modulate in the ictal state. Specifically, it has been suggested that the brain enters a more organized, lower complexity state prior to a seizure 33112. As the brain becomes more organized and nodes become more connected, the rank (number of linearly independent rows or columns) of the connectivity matrix drops. The SVD of a matrix highlights the rank of a matrix and also generates a weighted set of vectors that span the range space and null space of the matrix 103. Therefore, we can use SVD to measure the time-varying complexity of the brain by tracking the rank and its associated subspaces as a means to characterize non-ictal vs. ictal states. The SVD of the m×n connectivity matrix A is defined as $$A = USV^* = [u_1 \ u_2 \ \ldots \ u_m] \begin{bmatrix} \sigma_1 & & \\ & \ddots & \\ & & \sigma_r \\ & 0 & \end{bmatrix} \begin{bmatrix} v_1^* \\ v_2^* \\ \vdots \\ v_n^* \end{bmatrix} \quad (3)$$

where U is an m×m unitary ($UU^*=1$) matrix whose columns, $u_i$, are the eigenvectors of the matrix $AA^*$, V is an n×n unitary matrix whose columns, $v_i$, are the eigenvectors of the matrix $A^*A$, and * denotes the complex conjugate transpose operator. S is an m×n matrix whose first r diagonal entries $\sigma_1 \geq \sigma_2 \geq \ldots \geq \sigma_r$ are the nonzero singular values of A, with r being the rank of A 103. The first r columns of U span the column space of A and the first r rows of V span the row space of A. When m=n and A is square symmetric ($A=A^*$), the SVD reduces to the conventional eigenvalue decomposition, where the singular values are the square of the eigenvalues of A, $U=V^{-1}$, and the columns of U and V are the eigenvectors of A 103.

Figures 3A, 3B:
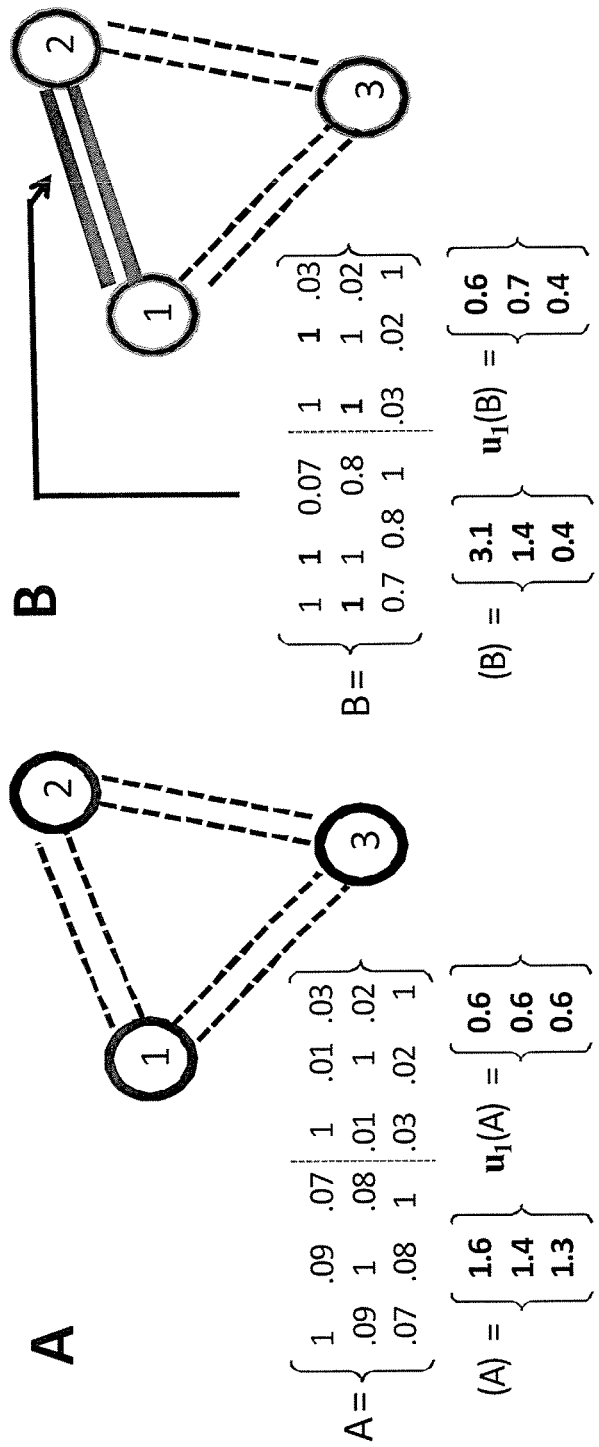
FIGS. 3A and 3B illustrate some concepts of the current invention. (A) three-node network with loose connections under 2 measures (2 edges between each pair of nodes) and the corresponding non-square connectivity matrix A, singular values, σ(A), and leading singular vector $u_1(A)$. (B) Nodes 1 and 2 of the network are strongly connected under both measures (thick edges). The first 2 singular values of the connectivity matrix B are much larger than the 3rd one and the first 2 components of first singular vector $u_1(B)$ are significantly larger in magnitude than the 3rd component.

An example is shown in FIG. 3. Here, two 3-node graphs are analyzed. In FIG. 3A, all nodes have similar weak connections (strength<1) under 2 measures (e.g. cross-power in 2 frequency bands). The SVD of the corresponding non square connectivity matrix, A, reveals that the matrix of this graph has full rank (3 comparable singular values in $\sigma(A)$). More physically, full rank here indicates the activity in the 3 nodes spans a 3 dimensional space, or has 3 degrees of freedom. If the strength between nodes 1 and 2 increases (FIG. 3B), one of the singular values of the corresponding connectivity matrix, B, becomes small in comparison to the other two, indicating that the rank of the matrix has approximately dropped to 2. This means that with the addition of one strong connection, the activity on the graph collapses to two dimensions and has becomes more "ordered". The singular vectors of graphs in FIG. 3 are given and indicate that the dominant direction of the vectors has also rotated in FIG. 3B.

The time dependent structure of the first singular vector direction of the connectivity matrix can be used as way to detect seizure onsets.

Example Results

Data: Four subjects with intractable epilepsy were surgically implanted with subdural grid and strip electrodes (26-75 channels, Ad-Tech® Medical Instrument Corporation, Racine, Wis.) for approximately one week before surgical resection of the focal region and monitored by clinicians for seizures and interictal epileptic activity. Electrodes are 4 mm diameter platinum contacts embedded in a silicone sheet with 2.3 mm exposed. Data were digitized and stored using an XLTEK® EMU128FS system (Natus Medical Incorporated, San Carlos, Calif.) with 250-500 Hz sampling frequency. Table I reports patient-specific information, number of electrodes included in this study, and electrode position, respectively. Board-certified electroencephalographers (up to 3) marked the unequivocal electrographic onset (UEO) by consensus of each seizure and the period between onset and termination. UEOs were used as the "Gold Standard" for evaluating the performances of the detection algorithm. Grid electrode recordings (iEEG) included in this study were made available with the written consent of the patients, in accordance with the protocol approved by the Institutional Review Boards at Brigham and Women's Hospital and Children's Hospital, Boston, Mass.

Multivariate SVD Statistics

The connectivity matrix was estimated using the cross-power in a specific frequency band (1) for each patient over consecutive overlapping windows (5 s-long window, 4 s overlap). See Table I. We computed connectivity in one frequency band for simplicity to initially construct our QD framework. The corresponding maximum singular value $\sigma_1$ and first singular vector $u_1$ are plotted in FIG. 4 for consecutive windows covering an ictal period.

TABLE I

Experimental setup.

| Patient ID | Seizure origin | Type of seizures | # iEEG channels | hours of recordings | Frequency band for $\sigma_1$ |
|---|---|---|---|---|---|
| 1 | T | CP | 34 | 40 | 13-30 Hz |
| 2 | T | TC | 28 | 47 | 4-7 Hz |
| 3 | F | CP | 44 | 47 | 13-30 Hz |
| 4 | O | SP | 26 | 34 | 13-30 Hz |

F = frontal lobe;
O = occipital lobe;
T = temporal lobe;
CP = complex partial;
SP = simple partial;
TC = tonic clonic.
For each patient, the frequency band was chosen by maximizing the distance between ictal vs. non-ictal GLM parameters (training data only).

The sequence of $\sigma_1$ has a consistent pattern across patients during the non-ictal, pre- and post-ictal states. The corresponding singular vector $u_1$ shows a leading direction before the seizure onset, which depends on both the patient and the location of the focal region. During a seizure, $\sigma_1$ rapidly increases compared to the non-ictal activity in the previous minutes, reaches a local maximum at approximately half of the ictal period (gray boxes, FIG. 4A-D), and then slowly decreases to smaller non-ictal values. The change in the dynamics of $\sigma_1$ is observed almost at the beginning of the hand-annotated seizure onset, while the return to the non-ictal condition is usually slower. Interestingly, after every seizure, $\sigma_1$ decreased below the average value achieved before the seizure and, then, increased to the pre-ictal values with a long drift (at least 2 hr, data not reported), which may be consistent with the definition of a post-ictal state given in 112.

Figures 4A, 4B, 4C, 4D:
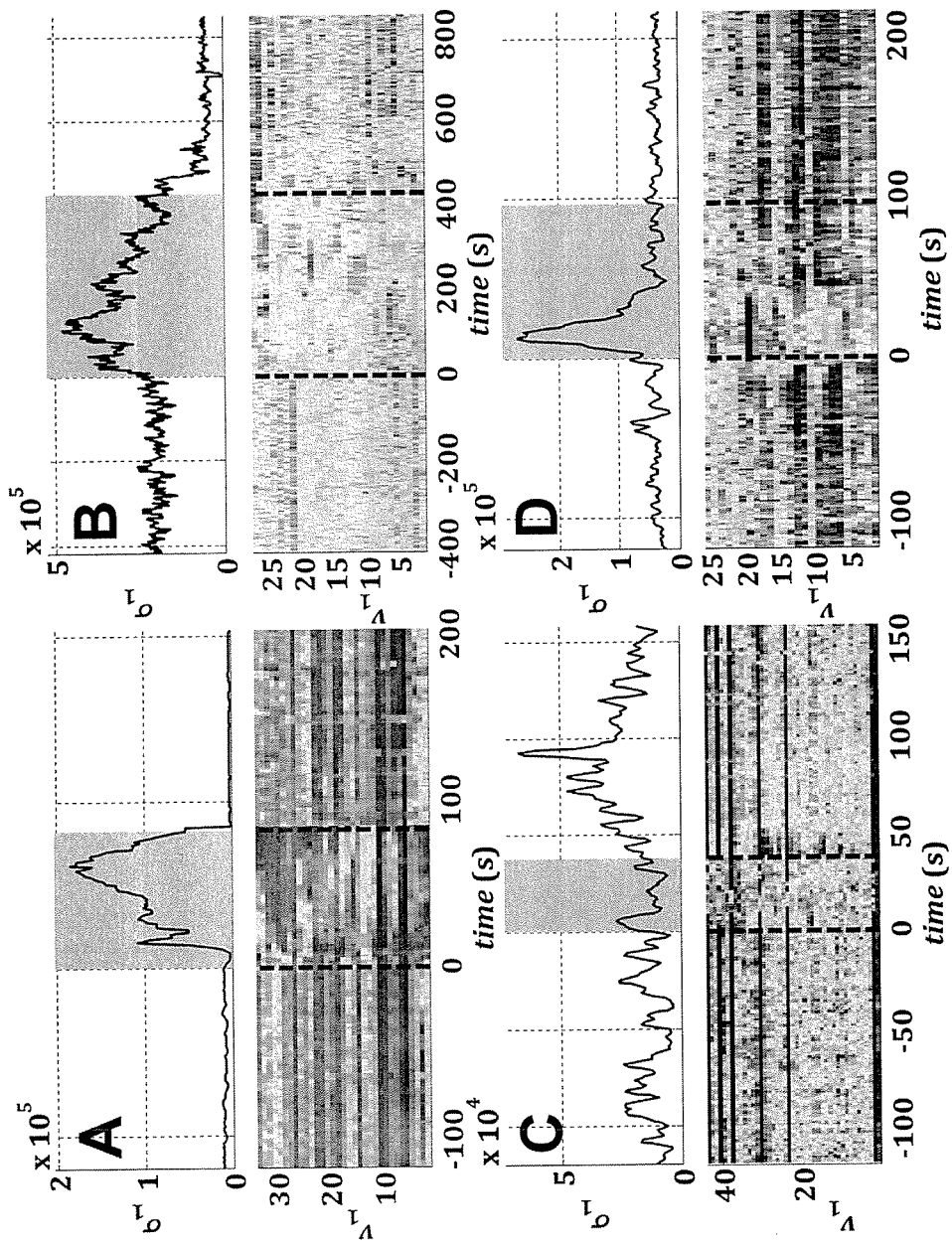
FIGS. 4A-4D provide first singular values $\sigma_2$ and correspondent vectors $u_1$ around an ictal period (gray background) in patient 1 (seizure $s_1$, A), 2 ($s_1$, B), 3 ($s_3$, C), and 4 ($s_3$, D).
Figures 4E, 4F:
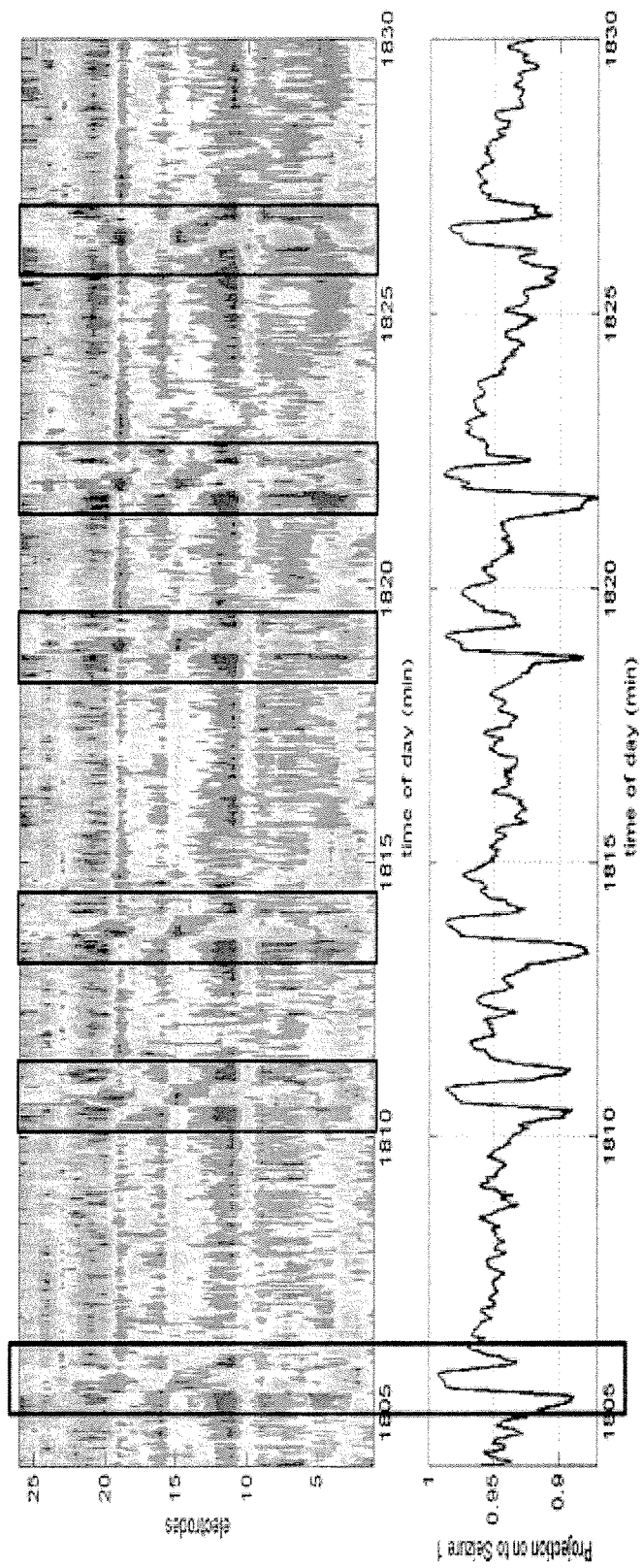
FIG. 4E shows $u_2$ vs. time for patient 4.
FIG. 4F provides average $u_2$ of the first seizure projected onto subsequent seizures.

The stereotypical dynamics of $\sigma_1$ was associated with a sudden change in the direction of the singular vector $u_1$. Furthermore, the new direction remained consistent across different seizures (FIG. 4E,F). Modulo a scaling factor, the dynamics of $\sigma_1$ and $u_1$ were similar in patients 1-2, and 4 (FIG. 4A,B,D), independently of the connectivity matrix being computed in different frequency bands. These dynamics were less clear in patient 3, where $\sigma_1$ showed slow oscillations independently of the seizure occurrence (FIG. 4C, top). However, at the seizure onset, the value of $\sigma_1$ first decreased, then rapidly rose to a local maximum, and finally drifted to baseline value, as did occur in the other patients.

The notion of connectivity (e.g. cross power) and the particular statistic computed from the connectivity matrix (e.g. $\sigma_1$) may not perform well for all types of seizures or all types of epilepsy. If needed, can use other connectivity measures (e.g. mutual information 111) and/or other matrix measures (e.g. spectral clusters [83]). Furthermore, there may be patients with independent multifocal onsets, which may be reflected by a connectivity matrix that changes periodically over time as seizures ping-pong back and forth between foci. To identify these cases, localization consistency will be measured across all seizures within a patient.

(Ii) Modeling the Evolution of Multivariate Statistics

In this example, we model the evolution of the maximum singular value statistic using an HMM. For any given patient, we assume that the maximum singular value computed at each second is generated by an HMM. In particular, at each stage $k \geq 0$, the brain is in one of m subclinical states, i.e., $x_k \in \{0, 1, \ldots, m-1\}$, which follows a Markov Chain 113, i.e.

$$Pr(x_{k+1}=j|x_k, x_{k-1}, \ldots, x_0) = Pr(x_{k+1}=j|x_k=i) \triangleq p_{ij} \text{ for all } i,j$$

$$\Sigma_{j=1}^{m-1} p_{ij} = 1 \forall i, \Sigma_{i=1}^{m} \mathcal{P}_i = 1 \quad (4)$$

where $\mathcal{P}_i \triangleq Pr(x_0 = i)$, $i = 0, 1, \ldots, m-1$, is the probability of starting in state i. For a fixed state i, we assume that the observations $z_k \triangleq \sigma_1(k)$, $k=1, 2, \ldots$ are generated according to a known history-dependent probability law $q_i(z|H_k) \triangleq Pr(z_k=z|x_k=i, H_k)$, where $H_k \triangleq \{z_0, z_1, \ldots z_{k-1}\}$ denotes the sequence of past observations. Note that the dependency of $z_k$ on previous observations accounts for temporal dependencies that exist in neural data 115116. The HMM is therefore uniquely defined by the triple $\{\mathcal{P}, \Sigma, q\}$, with $\mathcal{P} \triangleq [\mathcal{P}_0 \mathcal{P}_1 \ldots \mathcal{P}_{m-1}]$, $\Sigma_{i,j} \triangleq p_{ij}$, i,j=0, 1, ..., m-1, and $q \triangleq [q_0 \ldots q_{m-1}]$. See FIG. 5A.

For our QD framework, we may initially fit an m=2 state HMM on each patient, with state x=0 and x=1 denoting the non-ictal and ictal condition, respectively. The ictal state begins and ends with the unequivocal ictal onset and offset determined by clinicians. Early-ictal or pre-ictal conditions are subsumed in the non-ictal state as they may not exist in all patients. Since we will begin monitoring a patient in the non-ictal state 0, we set $\mathcal{P} = [1\ 0]$. We will also initially assume that the state transition probability matrix is $$\Sigma = \begin{bmatrix} 1-\rho & \rho \\ 0 & 1 \end{bmatrix}, \quad (5)$$

where $\rho$ will be estimated from training data via maximum likelihood estimation 114-116. The output probability law $q_x(z|H_k)$, $x=0,1$ will be estimated by combining generalized linear models (GLM) 117 and maximum likelihood estimation. Training data includes at least 3 hours of non-ictal data well before seizure (min 3 hr, max 12 hr before the seizure) and at least 1 ictal period.

Figures 5A, 5B, 5C:
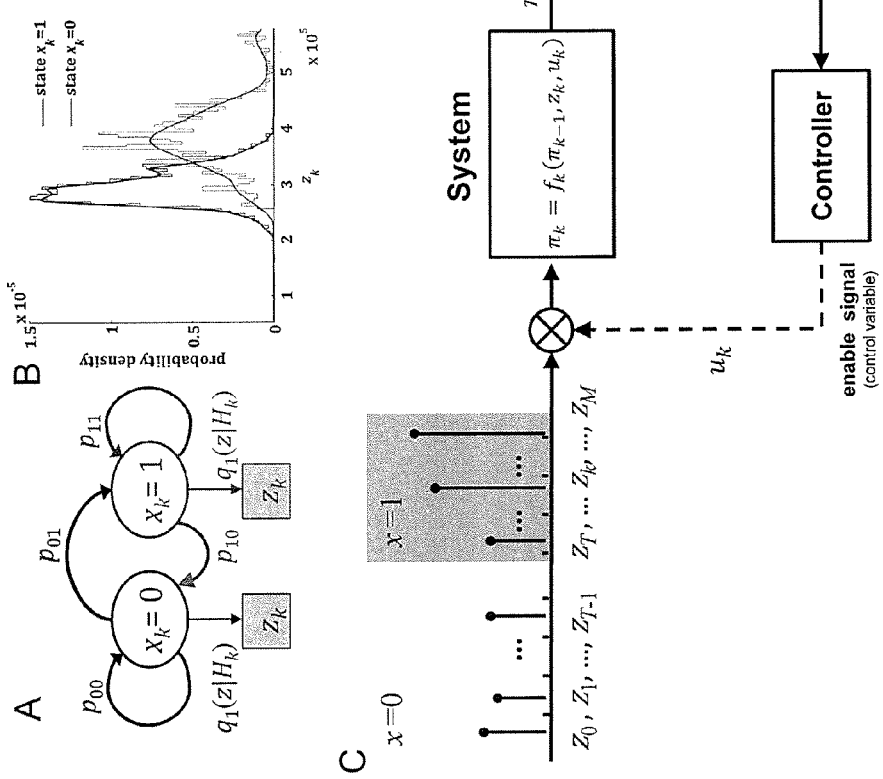
FIG. 5A is a schematic illustration of a m=2 state HMM according to an embodiment of the current invention.
FIG. 5B shows the sampling probability distribution function of the observations $z_k$ collected in state $x_k=0$ (non-ictal) and $x_k=1$ (ictal). Data collected from Patient 2 in the preliminary dataset.
FIG. 5C shows OSD formulated as a feedback control problem according to an embodiment of the current invention.
Figure 6:
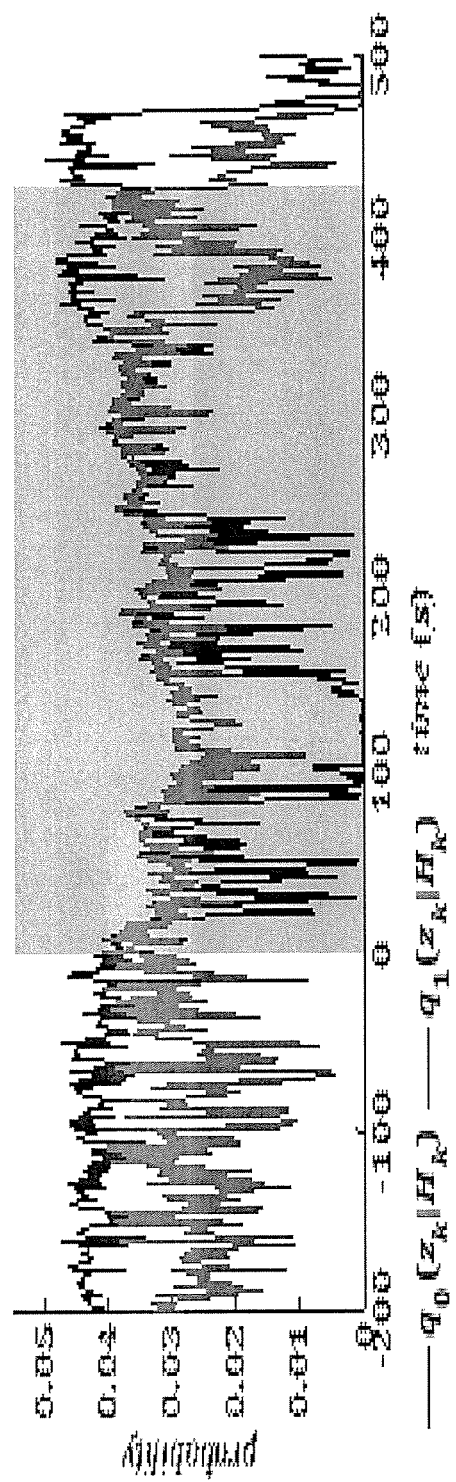
FIG. 6 shows history-dependent values of $q_0(z_k|H_k)$ and $q_2(z_k|H_k)$ at the onset of an annotated seizure (gray background).

Results. FIG. 5B and FIG. 6 show results for the HMM estimation. Although the mean value and the variance of $\sigma_1$ were different in the ictal versus non-ictal state, the sampling probability distribution functions overlap (FIG. 5B), which means that several of the same values of $\sigma_1$ were likely to be achieved both during the ictal and non-ictal states.

To better characterize the distribution of $\sigma_1$ in each state, we used a history-dependent model (see 102 for details) to describe the distribution of $\sigma_1$ (FIG. 6). At each stage k, this model modulates the probability of observing $\sigma_1(k)$ in each state based on the values of $\sigma_1$ in the last 15 s. The functions $q_0$ and $q_1$ (i) varied the probability of any given observation $\sigma_1$ at each stage k depending on the past observations, and (ii) had opposite dynamics in ictal vs. non-ictal state. For the computed sequence of $\sigma_1$ in each patient, $q_1(\cdot)$ was consistently larger than $q_0(\cdot)$ during ictal periods, but decreased during non-ictal periods (FIG. 6). In each patient, $q_0(\cdot)$ and $q_1(\cdot)$ were almost 0 right after every seizure, suggesting a post-ictal period characterized by a resetting of brain activity 112.

There may be reactivity of iEEG waveforms due to sleeping, moving etc. that impacts how the multivariate statistic evolves over time. To capture reactivity, it may needed to build an m-state HMM, where m>2, for each patient (e.g. m=3: non-ictal sleep, non-ictal awake, ictal). The methodology described above is easily extended to such cases.

(iii) Quickest Detection of Seizure Onsets

Next, we will (i) implement the QD framework, (ii) test the QD-based strategy on clinical data, and (iii) compare QD to a variety of existing OSD algorithms. We begin by deriving the QD framework and then describe other OSD algorithms that we will also implement for comparison. We then discuss results of the examples according to an embodiment of the current invention.

Because the state of an HMM is hidden, a Bayesian information state variable $\pi_k \triangleq Pr(x_k=1|z_k, H_k)$ can be introduced 119 in order to estimate how likely the transition from the non-ictal to ictal state is at each stage k. Note that $\pi_k$ is the a posteriori probability of being in state 1 at stage k and depends on the observations up to and including stage k. The evolution equation of $\pi_k$ is recursive and given by $$\pi_{k+1} = \frac{L_{k+1}[\pi_k + (1-\pi_k)p_{01}]}{(1-\pi_k)(1-p_{01}) + L_{k+1}[\pi_k + (1-\pi_k)p_{01}]} \triangleq \Phi(\pi_k, z_{k+1}, H_{k+1}) \quad (6)$$

where $q_x(z_0)$ is the probability of observing $z_0$ in state 0 at time $$k = 0, L_k \triangleq \frac{q_1(z_k|H_k)}{q_0(z_k|H_k)}$$

is the likelihood ratio, and Bayes' rule is applied. See 102 for details. Note that the evolution equation (6) depends on the likelihood ratio, $L_k$, between $q_1$ and $q_0$. The dependency of $q_1$ and $q_0$ on the history $H_k$ contributes to separating their dynamics, thus achieving a larger modulation of $L_k$ in ictal vs. non-ictal states. Consequently, this history-dependency makes $\pi_k$ more reliable as it achieves high values only around the actual seizure onset.

The quickest detection problem is an online decision problem, where at each stage k, we test the hypothesis $\mathcal{H} \triangleq \{$a seizure onset has occurred$\}$ conditioned on the observations $(H_k, z_k)$. We introduce the decision variable $u_k \in \{0,1\}$, where $u_k=0$ ($u_k=1$) denotes that the hypothesis $\mathcal{H}_0$ is rejected (accepted) at stage k. In this $$\pi_{k+1} = f(\pi_k, z_{k+1}, H_{k+1}, u_k) \triangleq \begin{cases} \Phi(\pi_k, z_{k+1}, H_{k+1}) & u_k = 0 \\ \text{terminate \& restart} & u_k = 1 \end{cases} \quad (7)$$

where the "terminate & restart" state implies that we restart the detection algorithm after a seizure is detected. With this setup, QD boils down to deciding when to switch from $u_k=0$ to $u_k=1$, thus claiming that a seizure has occurred. We will design a decision strategy that minimizes the following cost function, which weighs average detection delay and probability of a false positive:

$$\mathcal{J}_0 \triangleq (1-\gamma) E_{T|T_{QD}<T}\{T - T_{QD}\} + \gamma E_{T|T_{QD}>T}\{(T_{QD} - T)^2\} \quad (8)$$

where T and $T_{QD}$ are the actual and estimated seizure onset, respectively. T is unknown but its probability distribution is defined by the HMM transition probabilities, i.e., $$P(T = k) = (1 - p_{01})^{k-1} p_{01} \cdot E_{T|T_{QD}<T}\{\cdot\} \text{ and}$$

$$E_{T|T_{QD}>T}\{\cdot\}$$

denote the expected values of the distance between $T_{QD}$ and T for false positive ($T_{QD}<T$) and delayed detection ($T_{QD}>T$), respectively. Finally, the parameter $\gamma \in [0,1]$ allows the tradeoff of false positives and delayed detection, while the expected value $E_T\{\cdot\}$ accounts for the average temporal distance between actual and estimated seizure onset.

We then design the cost (8) as a function of the information state $\pi_k$ and decision variable $u_k$. Details are given in 102. Then, the optimal decision deals with choosing the stage $T_{QD}>0$ such that the policy ($u_1=0, u_2=0, \ldots, u_{T_{QD}-1}=0, u_{T_{QD}}=1$) minimizes the overall cost (8). One can interpret the minimization of (8) with respect to the variable $u_k$ given the evolution model (7), as an optimal feedback control problem where $u_k$ is the control variable (FIG. 5C). This formulation can be solved recursively via Dynamic Programming 83, and leads to the optimal quickest detection (QD) policy $$T_{QD} = \min\{0 < k < M | \pi_k > F_k(\pi_k, z_k, H_k)\} \quad (9)$$

where $F_k(\pi_k, z_k, H_k)$ is an adaptive threshold that depends on the current observation, history, and information state variable. The threshold $F_k(\cdot)$ is computed recursively and has no closed form and it decreases over time non-monotonically. Details can be obtained in 100102.

Example Results

For each patient, we compare the QD policy to a classical Bayesian estimator (BE) [119], which is widely used in the field of change point detection [33][119], and a heuristic threshold based detector (HT), where the threshold is chosen heuristically. The formulae for the estimated seizure onset with each of these predictors are: BE: $T_{BE} \triangleq \min\{k>0|\pi_k>0.5\}$ and HT: $T_{HT} \triangleq \min\{k>0|z_k>\bar{h}\}$, where the threshold $\bar{h}$ is fixed heuristically. For each detection policy, we measure the delay between each estimated seizure onset time and the unequivocal electrographic onset [120], which will be annotated by the epileptologists. We can also evaluate the number of true positives (TP), false positives (FP), and false negatives (FN) per patient, where each decision can be classified as TP or FP if an unequivocal onset occurs within a window W from the detection time or not. W was initially be set to 20 s to be comparable to [60]. An onset not detected is classified as FN. Finally, given TP, FP, and FN, two measures can be evaluated for each patient: (i) the false positive rate (FPR), which is the number of FP/hr, and the "sensitivity" (S), which is the ratio between TP and TP+FN. For each of these measures, we determine whether the results achieved with the QD policy and any other method are significantly different from the chance-level detection (i.e., random generator of warnings as in [121]) and whether FPR and S with QD are significantly lower than with the other methods (t-test). We can finally evaluate the sensitivity to changes of W as well as QD performance for different trade-off gains $\gamma$ in (10).

TABLE II

Performance Analysis.

| | | | QD | | | | | BE | | | | | HT | | | |
|---|---|---|---|---|---|---|---|---|---|---|---|---|---|---|---|---|
| | | | Specificity | | Sensitivity | | | Specificity | | Sensitivity | | | Specificity | | Sensitivity | |
| | Patient | Seizures | FP | FPR (FP/h) | FN | TP | $|T_s - T|$ (s) | FP | FPR (FP/h) | FN | TP | $|T_s - T|$ (s) | FP | FPR (FP/h) | FN | TP | $|T_s - T|$ (s) |
| Training | 1 | 1 | 0 | 0 | 0 | 1 | 18 | 0 | 0 | 0 | 1 | 16 | 8 | 2.67 | 0 | 1 | 14 |
| | 2 | 1 | 0 | 0 | 0 | 1 | 19 | 0 | 0 | 0 | 1 | 16 | 8 | 2.67 | 0 | 1 | 20 |
| | 3 | 1 | 3 | 1 | 0 | 1 | 10 | 3 | 1 | 0 | 1 | 7 | 8 | 2.67 | 1 | 0 | n.a. |
| | 4 | 2 | 0 | 0 | 0 | 2 | 9 | 0 | 0 | 0 | 2 | 7 | 0 | 0 | 0 | 2 | 5 |
| Validation | 1 | 1 | 6 | 0.16 | 0 | 1 | 15 | 6 | 0.16 | 0 | 1 | 14 | 42 | 1.14 | 0 | 1 | 12 |
| | 2 | 2 | 7 | 0.16 | 0 | 2 | 31 | 11 | 0.25 | 0 | 2 | 33 | 13 | 0.30 | 0 | 2 | 14.5 |
| | 3 | 3 | 130 | 2.95 | 0 | 3 | 13.7 | 320 | 7.27 | 0 | 3 | 10.7 | 75 | 1.71 | 3 | 0 | n.a. |
| | 4 | 22 | 71 | 2.29 | 0 | 22 | 11.8 | 138 | 4.45 | 0 | 22 | 9.7 | 277 | 8.94 | 0 | 22 | 5.8 |

Figures 7A, 7B:
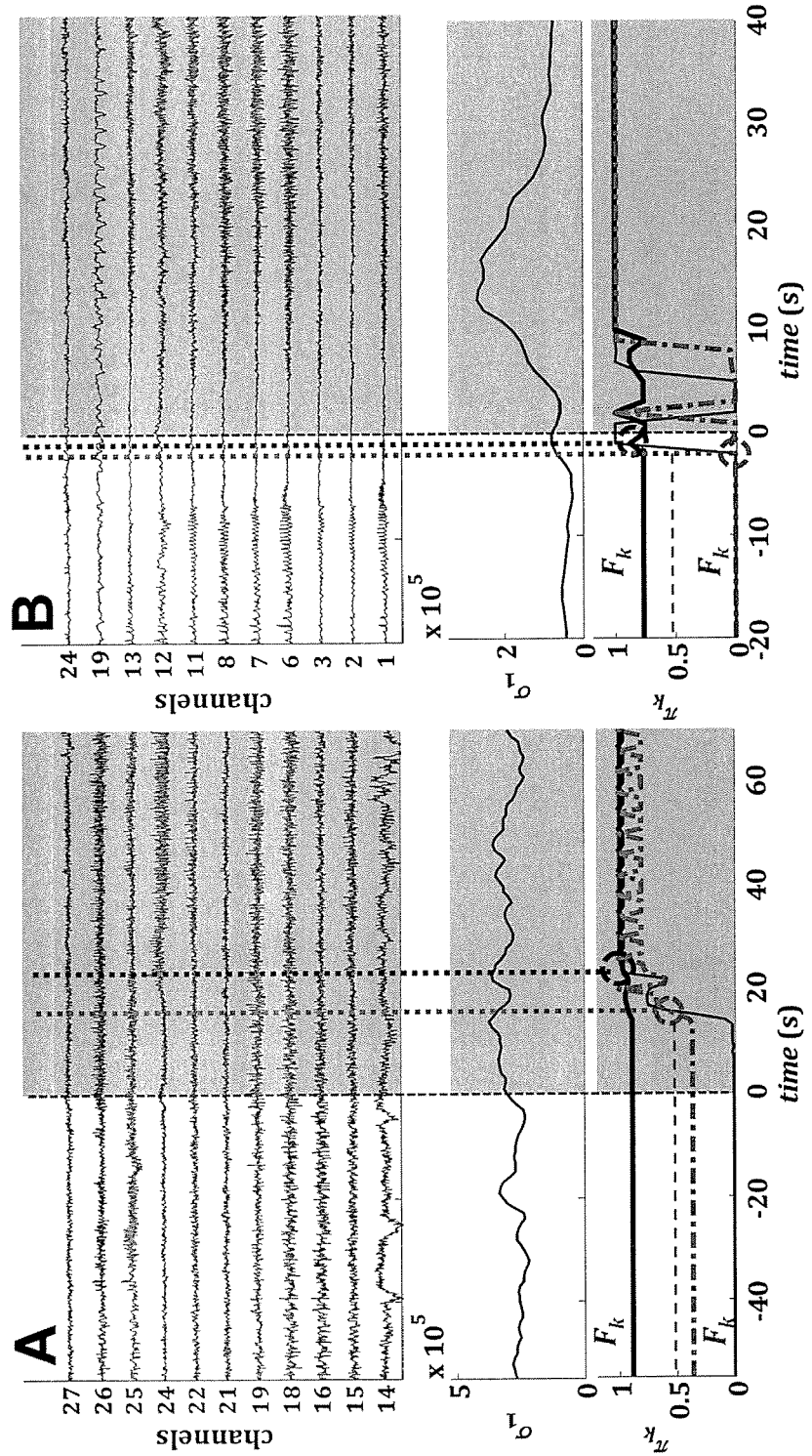
FIGS. 7A and 7B provide QD on validation data according to an embodiment of the current invention. The electrographic onset (red line), the correspondent QD estimation (circles), and threshold $F_k$ (green and blue lines for different values of parameter γ which trades off specificity/delay) for Patient 2 (A) and 4(B). Plots for seizures $s_3$ in both patients. In bottom plots, horizontal dashed black line is threshold for the BE detector.

FP = false positive; TP = true positive; FN = false negative; FPR = false positive rate; n.a. = not available Table II and FIG. 7 report results for the QD policy vs. the BE and HT detectors. QD achieved significantly fewer false positives than the Bayesian and threshold-based detector (min. 36% less; max. 85% less; mean: 58% less), while achieving 100% sensitivity in every patient. QD delays were comparable and in some cases slightly larger than delays of other detectors. However, FIG. 7A shows that for patient 2, by increasing the penalty for detection delay in (11) (i.e., increasing γ), QD reduced delays to values achieved by BE (16 s, green lines), while maintaining a lower number of FPs (7 vs. 11). For patient 4, by decreasing γ, QD achieved higher robustness to early modulations in the probability $\pi_k$, due to abrupt spikes in the sequence of $\sigma_1$ and QD decreased the number of FPs and detect a seizure with less anticipation (FIG. 7B).

QD results in significantly fewer FPs than other OSD methods, however, the detection delays, are comparable to those produced by other OSD methods. One can also explore penalizing other functions of the detection delay ($T_{QD}$-T) in the cost function (8) to reduce these delays according to other embodiments of the current invention. For example, one can allow this penalty to grow exponentially ($e^{IT_{QD}-r)}$) and as long as the function is a non-decreasing function of the delay, the QD method will hold.

REFERENCES 1. de Boer H M, Mula M, Sander J W (2008) The global burden and stigma of epilepsy. *Epilepsy Behav.* 12:540-546.
2. Bourgeois, B. F. D., Prensky, A. L., Palkes, H. S., Talent, B. K., & Busch, S. G. ( ). Intelligence in epilepsy: A prospective study in children. Annals of Neurology, 1983, 14: 438-444.
3. Austin, J. K., Harezlak, J., Dunn, D. W., Huster, G. A., Rose, D. F., & Ambrosius, W. T. Behavior problems in children before first recognized seizures. Pediatrics, 2001, 107(1):115-122.
4. Hoare P. The development of psychiatric disturbance among school children with epilepsy. Dev Med Child Neurol 1984, 26: 23-4.
5. Seidenberg M, Beck N, Geisser M, Giordani B, Sackellares J C, Berent S et al. Academic achievement of children with epilepsy. *Epilepsia* 1986, 27: 753-759.
6. Leonardi M, Ustun T B (2002) The global burden of epilepsy. *Epilepsia* 43:S21-S25.
7. Sander J W (2003) The epidemiology of epilepsy revisited. *Curr Opin Neurol.* 16:165-170.
8. Theodore W H, Spencer S, Wiebe S, et al. (2006) Epilepsy in North America: a report prepared under the auspices of the global campaign against epilepsy, the International Bureau for Epilepsy, the International League Against Epilepsy, and the World Health Organization. *Epilepsia* 47:1700-1722.
9. Fisher R S, van Emde Boas S, Blume W, Elger C, et al. (2005) Epileptic seizures and epilepsy: definitions proposed by the international league against epilepsy (ILAE) and the international bureau for epilepsy (IBE). *Epilepsia* 46:470-472.
10. Ben-Jacob E, Boccaletti S, Pomyalov A, Procaccia I., Towle V L (2007) Detecting and localizing the foci in human epileptic seizures. Chaos 17:043113.
11. Elger C E, Schmidt D (2008) Modern management of epilepsy: a practical approach. *Epilepsy Behav.* 12:501-539.
12. Perucca E, Kwan P (2005) Overtreatment in epilepsy. How it occurs and how it can be avoided. *CNS Drugs* 19:897-908.
13. Schmidt D (2009) Drug treatment of epilepsy: options and limitations. *Epilepsy Behav.* 15:56-65.
14. Kanemoto K, Tadokoro Y, Oshima T (2010) Violence and postictal psychosis: a comparison of postictal psychosis, inter-ictal psychosis, and postictal confusion. *Epilepsy Behav.* 19:162-166.
15. Nashef L, Fish D R, Garner S, Sander J W, Shorvon S D (1995) Sudden death in epilepsy: a study of incidence in a young cohort with epilepsy and learning difficulty. *Epilepsia* 36:1187-1194.
16. Nilsson L, Tomson T, Farahmand B Y, Diwan V, Persson P G (1997) Cause-specific mortality in epilepsy: a cohort study of more than 9,000 patients once hospitalized for epilepsy. *Epilepsia* 38: 1062-1068.
17. Cockerell O C, Johnson A L, Sander J W, Hart Y M, Goodridge D M, Shorvon S D. Mortality from epilepsy: results from a prospective population-based study. Lancet. Oct. 1 1994; 344(8927):918-21.
18. Olafsson E, Hauser W A, Gudmundsson G. Long-term survival of people with unprovoked seizures: a population-based study. Epilepsia. January 1998; 39(1):89-92.
19. Loiseau J, Picot M C, Loiseau P. Short-term mortality after a first epileptic seizure: a population-based study. Epilepsia. October 1999; 40(10):1388-92.
20. Lindsten H, Nyströ L, Forsgren L. Mortality risk in an adult cohort with a newly diagnosed unprovoked epileptic seizure: a population-based study. Epilepsia. November 2000; 41(11):1469-73.
21. Lhatoo S D, Sander J W. Cause-specific mortality in epilepsy. Epilepsia. 2005; 46 Suppl 11:36-9.
22. Téllez-Zenteno J F, Ronquillo L H, Wiebe S. Sudden unexpected death in epilepsy: evidence-based analysis of incidence and risk factors. Epilepsy Res. June 2005; 65(1-2):101-15.
23. Engel J (1994) Epilepsy surgery. *Curr Opin Neurol.* 7:140-147.
24. Lee S K, Lee S Y, Kim K, Hong K S, Lee D S, Chung C K (2005) Surgical outcome and prognostic factors of cryptogenic neocortical epilepsy. *Ann Neurol.* 58:525-532.
25. Fisher R, Salanova V, Witt T, et al. (2010) Electrical stimulation of the anterior nucleus of thalamus for treatment of refractory epilepsy. *Epilepsia* 51:899-908.
26. Jiruska P, Powell A D, Deans J K, Jefferys J G (2010) Effects of direct brain stimulation depend on seizure dynamics. *Epilepsia* 51:S93-S97.
27. Jobst B C, Darcey T M, Thadani V M, Roberts D W (2010) Brain stimulation for the treatment of epilepsy. *Epilepsia* 51:S88-S92.
28. Morrell M. (2006) Brain stimulation for epilepsy: Can scheduled or responsive neurostimulation stop seizures? *Curr Opin Neurol.* 19:164-168.
29. Anderson W S, Kossoff E H, Bergey G K, Jallo G I (2008) Implantation of a responsive neurostimulator device in patients with refractory epilepsy. *Neurosurg Focus.* 25:E12.
30. Fountas K N, Smith J R, Murro A M, Politsky J, et al. (2005) Implantation of a closed-loop stimulation in the management of medically refractory focal epilepsy: a technical note. *Stereotact Funct Neurosurg.* 83:153-158.
31. Morrell M, Hirsch L, Bergey G K, Barkley G, et al. (2008) Long-term safety and efficacy of the RNS™ system in adults with medically intractable partial onset seizures. *Proc. American Epilepsy Society Annual Meeting.* Abstract No. 8536. www.aesnet.org.
32. Morrell M J (2011): On behalf of the RNS System in Epilepsy Study Group. Responsive cortical stimulation for the treatment of medically intractable partial epilepsy. Neurology; 77:1295-1304.

33. Ben-Jacob E, Doron I, Gazit T, Rephaeli E, Sagher O, Towle V L (2007b) Mapping and assessment of epileptogenic foci using frequency-entropy templates. Phys. Rev. E 76:051903.
34. Bettus G, Wendling F, Guye M, Valton L, Regis J, Chauvel P, Bartolomei F (2008) Enhanced EEG functional connectivity in mesial temporal lobe epilepsy. Epilepsy Res. 81:58-68.
35. Franaszczuk P J, Berge G K, Kamifiski M J (1994) Analysis of mesial temporal seizure onset and propagation using the directed transfer function method. Electroenceph. Clin. Neurophysiol. 91:413-427.
36. Franaszczuk P J, Bergey G K (1998) Application of the directed transfer function method to mesial and lateral onset temporal lobe seizures. Brain Topogr. 11(1):13-21.
37. Gotman J (1983) Measurements of small time differences between EEG channels: method and application to epileptic seizure propagation. Electroenceph. clin. Neurophysiol., 56:501-514.
38. Luders H O, Awad I (1992) Conceptual considerations. In Epilepsy Surgery. Raven Press, New York pgs 51-62.
39. Lai Y-C, Harrison M, Frei M, Osorio I (2004) Controlled test for predictive power of Lyapunov exponents: Their inability to predict epileptic seizures. Chaos, 14(3):630-642.
40. Osterhage H, Mormann F, Wagner T, Lehnertz K (2008) Detecting directional coupling in the human epileptic brain: Limitations and potential pitfalls. Phys Rev. E, 77:011914.
41. Sabesan S, Good L B, Tsaklis K S, Spanias A, Treiman D M, Iasemidis L D (2009) Information flow and application to epileptogenic focus localization from intracranial EEG. IEEE Trans. Neural Sys. Rehab. Eng. 17(3):244-253.
42. Schevon C A, Cappell J, Emerson R, Isler J, Grieve P, Goodman R, Mckhann G, Weiner H, Doyle W, Kuzniecky R, Devinsky O, Gilliam F (2007) Cortical abnormalities in epilepsy revealed by local EEG synchrony. NeuroImage 35:140:148.
43. Staniek M, Lehnertz K (2008) Symbolic transfer entropy. Phys Rev. Lett. 100:158101.
44. Warren C P, Hu S, Stead M, Brinkmann B H, Bower M R, Worrell G A (2010) Synchrony in normal and focal epileptic brain: the seizure onset zone is functionally disconnected. J. Neurophysiol. 104:3530-3539.
45. Zaveri H P, Pincus S M, Goncharva I, Duckrow R B, Spencer D, Spencer S (2009) Localization-related epilepsy exhibits significant connectivity away from the seizure-onset area. NeuroReport, 20:891-895.
46. Andrzejak R G, Chicharro D, Lehnertz K, Mormann F (2011) Using bivariate signal analysis to characterize the epileptic focus: The benefit of surrogates. Phys. Rev. E 83:046203.
47. Alarcon G, Garcia Seoane J, Binnie C D, Martin Miguel M C, Juler J, Polkey C E, Elwes R D C, Ortiz Blasco J M (1997) Origin and propagation of interictal discharges in the acute electrocorticogram Implications for pathophysiology and surgical treatment of temporal lobe epilepsy. Brain 120:2259-2282.
48. Palus M, Komarek V, Hrncir Z, Sterbova K (2001) Synchronization as adjustment of information rates: Detection from bivariate time series. Phys Rev. E 63:046211.
49. R. Fisher, V. Salanova, T. Witt, R. Worth, T. Henry, R. Gross, K. Oommen, I. Osorio, J. Nazzaro, D. et al. (2010) Electrical stimulation of the anterior nucleus of thalamus for treatment of refractory epilepsy. Epilepsia. March 17.
50. Gotman J, Gloor P. (1976) Automatic recognition and quantification of interictal epileptic activity in the human scalp EEG. Electroenceph. Clin. Neurophysiol. 41:513-529.
51. Gotman J. (1982) Automatic recognition of epileptic seizures in the EEG. Electroenceph. Clin. Neurophysiol. 54:530-540.
52. Osorio I, Frei M G, Wilkinson S B. (1998) Real-time automated detection and quantitative analysis of seizures and short-term prediction of clinical onset. Epilepsia 39:615-627.
53. Osorio I, Frei M G, Giftakis J, Peters T, et al. (2002) Performance reassessment of a real-time seizure-detection algorithm on long ECoG series. Epilepsia 43:1522-1535.
54. Haas S M, Frei M, Osorio I. (2007) Strategies for adapting automated seizure detection algorithms. Med Eng Phys. 29:895-909.
55. Osorio I, Frei M G. (2009) Real-time detection, quantification, warning, and control of epileptic seizures: the foundations for a scientific epileptology. Epilepsy Behav. 16:391-396.
56. Jerger K, Netoff T I, Francis J T, Sauer T, et al. (2001) Early seizure detection. J. Clin. Neurophysiol. 18:259-268.
57. Esteller R, Echauz J, D'Alessandro M, Worrell G, et al. (2005) Continuous energy variation during the seizure cycle: towards an on-line accumulated energy. Clin Neurophysiol. 116:517-526.
58. Gardner A B, Worrell G A, Marsh E, Dlugos D, Litt B. (2007) Human and automated detection of high-frequency oscillations in clinical intracranial EEG recordings. Clin Neurophysiol. 118:1134-1143.
59. Khan Y U, Gotman J. (2003) Wavelet based automatic seizure detection in intracerebral electroencephalogram. J. Clin Neurophysiol. 114:898-908.
60. Grewal S, Gotman J. (2005) An automatic warning system for epileptic seizures recorded on intracerebral EEGs. Clin. Neurophysiol. 116:2460-2472.
61. Saab M E, Gotman J. (2005) A system to detect the onset of epileptic seizures in scalp EEG. Clin Neurophysiol. 116:427-442.
62. Alkan A, Koklukaya E, Subasi A. (2005) Automatic seizure detection in EEG using logistic regression and artificial neural network. J Neurosci Methods 148:167-176.
63. van Putten M J, Kind T, Visser F, Lagerburg V. (2005) Detecting temporal lobe seizures from scalp EEG recordings: a comparison of various features. Clin Neurophysiol. 116:2480-2489.
64. Wilson S B. (2005) A neural network method for automatic and incremental learning applied to patient-dependent seizure detection. Clin Neurophysiol. 116:1785-1795.
65. Wilson S B. (2006) Algorithm architectures for patient dependent seizure detection. Clin Neurophysiol 117:1204-1216.
66. Srinivasan V, Eswaran C, Sriraam N. (2007) Approximate entropy-based epileptic EEG detection using artificial neural networks. IEEE Trans Inf Technol Biomed. 11:288-295.

67. Chan A M, Sun F T, Boto E H, Wingeier B M. (2008) Automated seizure onset detection for accurate onset time determination in intracranial EEG. *Clin Neurophysiol.* 119:2687-2696.
68. Aarabi A, Fazel-Rezai R, Aghakhani Y. (2009) A fuzzy rule-based system for epileptic seizure detection in intracranial EEG. *Clin Neurophysiol.* 120:1648-1657.
69. Tito M, Cabrerizo M, Ayala M, Jayakar P, Adjouadi M. (2009) Seizure detection: an assessment of time- and frequency-based features in a unified two-dimensional decisional space using nonlinear decision functions *J Clin Neurophysiol.* 26:381-391.
70. Minasyan G R, Chatten J B, Chatten M J, Hamer R N. (2010) Patient-specific early seizure detection from scalp electroencephalogram. *J Clin Neurophysiol.* 27:163-178.
71. Temko A, Thomas E, Marnane W, Lightbody G, Boylan G. (2011) EEG-based neonatal seizure detection with Support Vector Machines. *Clin Neurophysiol.* 122:464-473.
72. Shoeb A, Edwards H, Connolly J, Bourgeois B, Treves S T, Guttag J. (2004) Patient-specific seizure onset detection. *Epilepsy Behav.* 5:483-498.
73. Ghosh-Dastidar S, Adeli H, Dadmehr N. (2007) Mixed-band wavelet-chaos-neural network methodology for epilepsy and epileptic seizure detection. *IEEE Trans Biomed Eng.* 54:1545-1551.
74. Ghosh-Dastidar S, Adeli H, Dadmehr N. (2008) Principal component analysis-enhanced cosine radial basis function neural network for robust epilepsy and seizure detection. *IEEE Trans Biomed Eng.* 55:512-518.
75. Meier R, Dittrich H, Schulze-Bonhage A, Aertsen A. (2008) Detecting epileptic seizures in long-term human EEG: a new approach to automatic online and real-time detection and classification of polymorphic seizure patterns. *J Clin Neurophysiol.* 25:119-131.
76. Abibullaev B, Kim M S, Seo H D. (2010) Seizure detection in temporal lobe epileptic EEGs using the best basis wavelet functions. *J Med Syst.* 34:755-765.
77. Guo L, Rivero D, Dorado J, Rabuñal J R, Pazos A. (2010) Automatic epileptic seizure detection in EEGs based on line length feature and artificial neural networks. *J. Neurosci. Methods* 191:101-109.
78. Guo L, Rivero D, Pazos A. (2010) Epileptic seizure detection using multiwavelet transform based approximate entropy and artificial neural networks. *J Neurosci Methods* 193:156-163.
79. Shoeb A, Pang T, Guttag J, Schachter S (2009) Non-invasive computerized system for automatically initiating vagus nerve stimulation following patient-specific detection of seizures or epileptiform discharges. *Int J Neural Syst.* 19:157-172.
80. Lee H C, van Drongelen W, McGee A B, Frim D M, Kohrman M H. (2007) Comparison of seizure detection algorithms in continuously monitored pediatric patients. *J Clin Neurophysiol* 24:137-146.
81. Shiryayev A N. (1963) On optimum methods in quickest detection problems. *Theory Probab Appl.* 8: 22-46.
82. Poor H V, Hadjiliadis O. (2008) *Quickest Detection.* Cambridge, UK: Cambridge Univ. Press.
83. Bertsekas D P. (2005) *Dynamic Programming and Optimal Control.* Belmont, Mass.: Athena Scientific.
84. Jung W Y, Pacia S V, Devinsky O (1999) Neocortical temporal lobe epilepsy: intracranial EEG features and surgical outcome. *J. Clin. Neurophysiol.*, 16(5):419-428.
85. Iasemidis L D, Shiau D-S, Sackellares J C, Pardalos P M, Prasad A. (2004) Dynamical resetting of the human brain at epileptic seizures: application of nonlinear dynamics and global optimization techniques. *IEEE Trans Biomed Eng.* 51:493-506.
86. Wilke C, Worrell G, He B (2011) Graph analysis of epileptogenic networks in human partial epilepsy. Epilepsia, 52(1):84-93.
87. Bullmore E, Sporns O (2009) Complex brain networks: graph theoretical analysis of structural and functional systems. Nat Rev. Neurosci. 10:186-198.
88. Kramer M A, Eden U T, Kolaczyk E D, Zepeda R, Eskandar E N, Cash S (2010) Coalescence and fragmentation of cortical networks during focal seizures. J. Neurosci. 30(30):10076-10085.
89. Matsuoka L, Spencer S (1993) Seizure localization using subdural grid electrodes. Epilepsia, 34(6):8.
90. Muller M, Baier G, Galka A, Stephani U, Muhle H (2005) Detection and characterization of changes of the correlation structure in multivariate time series. Phys. Rev. E 71:046116.
91. Ponten S C, Bartolomei F, Stam C J (2007) Small-world networks and epilepsy: Graph theoretical analysis of intracerebrally recorded mesial temporal lobe seizures. Clin. Neurophys. 118:918-927.
92. Ponten S C, Douw L, Bartolomei F, Reijneveld J C, Stam C J (2009) Indications for network regularization during absence seizures: Weighted and unweighted graph theoretical analyses. Exp. Neurology 217:197-204.
93. Baier G, Muller M, Stephani U, Muhle H (2007) Characterizing correlation changes of complex pattern transitions: The case of epileptic activity. *Phys. Let. A,* 363:290-296.
94. Rummel C, Baier G, Muller M (2007) The influence of static correlations on multivariate correlation analysis of the EEG. J. Neurosci. Meth. 166:138-157.
95. Rummel C, Muller M, Baier G, Amor F, Schindler K (2010) Analyzing spatio-temporal patterns of genuine cross-correlations. J. Neurosci. Meth. 191:94-100.
96. Rummel C, Abela E, Muller M, Hauf M, Scheidegger O, Wiest R, Schindler K (2011)
Uniform approach to linear and nonlinear interrelation patterns in multivariate time series. Phys. Rev. E 83:066215.
97. Schindler K, Leung H, Elger C E, Lehnertz K (2007) Assessing seizure dynamics by analysing the correlation structure of multichannel intracranial EEG. Brain 130:65-77.
98. Schindler K A, Bialonski S, Horstmann M T, Elger C E, Lehnertz K (2008) Evolving functional network properties and synchronizability during human epileptic seizures. Chaos 18:033119.
99. Schindler K, Amor F, Gast H, Muller M, Stibal A, Mariani L, Rummel C (2010) Peri-ictal correlation dynamics of high-frequency (80-200 Hz) intracranial EEG. Epilepsy Res. 89:72-81.
100. Newman M J (2010) Networks: An Introduction. 720 pgs. Oxford University Press, USA.
101. Sarma S V, Santaniello S (2011) Quickest detection of state-transition in point processes: application to neuronal activity. *Proc. 18th IFAC World Conference.* Milan, ITALY, Aug. 29-Sep. 2, 2011.

102. Santaniello S, Burns S P, Madsen J, Singer J, Anderson W S, Sarma S V (2011) Quickest Detection of Seizure Onsets in Drug-Resistant Patients: An Optimal Control Approach. *Epilepsy Behav.* (*Accepted for publication*).
103. Golub H G, Van Loan C F. (1996) *Matrix Computations*. 3rd edition. Baltimore, Md.: Johns Hopkins University Press.
104. Shoeb A (2009) *Application of Machine Learning to Epileptic Seizure Onset Detection and Treatment*. PhD Thesis, Massachusetts Institute of Technology.
105. Goldberger A L, Amaral L A N, Glass L, Hausdorff J M, et al. (2000) PhysioBank, PhysioToolkit, and PhysioNet: Components of a new research resource for complex physiologic signals. *Circulation* 101:e215-e220.
106. Bernhardt B C, Chen Z, He Y, Evans A C, Bernasconi N. (2011) Graph-theoretical analysis reveals disrupted small-world organization of cortical thickness correlation networks in temporal lobe epilepsy. *Cereb Cortex* 21:2147-2157.
107. Schindler K A, Bialonski S, Horstmann M T, Elger C E, Lehnertz K. (2008) Evolving functional network properties and synchronizability during human epileptic seizures. *Chaos* 18:033119.
108. Kramer M A, Kolaczyk E D, Kirsh H E (2008) Emergent network topology at seizure onset in humans. *Epilepsy Res.* 79:173-186.
109. Newman M E J. (2010) *Networks: An Introduction*. Cambridge, UK: Oxford University Press.
110. Oppenheim A V, Schafer R W. (1999) *Discrete-Time Signal Processing*. Upper Saddle River, N.J.: Prentice-Hall.
111. Cover T M, Thomas J A (2006) *Elements of Information Theory*. 2nd edition, Wiley-Interscience, New York, N.Y.
112. Liu C C, Pardalos P M, Chaovalitwongse W A, Shiau D S, et al (2008) Quantitative complexity analysis in multi-channel intracranial EEG recordings from epilepsy brains. *J Comb Optim.* 15:276-286.
113. Elliott R J, Aggoun L, Moore J B. (1995) *Hidden Markov Models. Estimation and Control*. New York, N.Y.: Springer.
114. Brown E N, Barbieri R, Eden U T, Frank L M. (2003) Likelihood methods for neural data analysis. In: *Computational neuroscience: a comprehensive approach* (J. Feng, ed), pp. 253-286. London, UK: CRC.
115. Coleman T P, Sarma S V (2010) A computationally efficient method for nonparametric modeling neural spiking activity with point processes. *Neural Comp.* 22:2002-2030.
116. Sarma S V, Cheng M, Williams Z, Hu R, Eskandar E, Brown E N (2010) Using point process models to compare neuronal activity in sub-thalamic nucleus of Parkinson's patients and a healthy primate. *IEEE Trans Biomed Eng.* 57:1297-1305.
117. McCullagh P, Nelder J A. (1990) *Generalized linear models*. 2nd edition, Boca Raton, Fla.: CRC.
118. Akaike H. (1974) A new look at the statistical model identification. *IEEE Trans Aut Control.* 19:716-723.
119. Berger J O. (1985) *Statistical Decision Theory and Bayesian Analysis*. 2nd edition. New York, N.Y.: Springer.
120. Risinger M, Engel J J, VanNess P, Henry T, Crandall P. (1989) Ictal localization of temporal seizures with scalp-sphenoidal recordings. *Neurology* 39:1288-1293.
121. Sackellares J C, Shiau D S, Principe J C, Yang M C, et al. (2006) Predictability analysis for an automated seizure prediction algorithm. *J Clin Neurophysiol.* 23:509-520.
122. Yu A J. Optimal change-detection and spiking neurons. Neural Information Processing Systems Conference (NIPS) 2006: 1545-1552.

The embodiments discussed in this specification are intended to explain concepts of the invention. However, the invention is not intended to be limited to the specific terminology selected and the particular examples described. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A neurostimulation device, comprising:
a plurality of electrodes adapted to be electrically connected to a subject to receive multichannel electrical signals from a brain of said subject;
a multichannel seizure detection unit electrically connected to said plurality of electrodes to receive said multichannel electrical signals; and
a neurostimulation unit in communication with said multichannel seizure detection unit,
wherein said plurality of electrodes are at least three electrodes such that said multichannel electrical signals are at least three channels of electrical signals,
wherein said multichannel seizure detection unit detects a presence of a seizure based on multichannel statistics from said multichannel electrical signals including higher order combinations than two-channel combinations,
wherein said multichannel seizure detection unit is configured to detect said presence of said seizure based on optimizing a cost function, and
wherein said cost function is dependent on a time delay between an actual seizure and a prediction of said seizure.

2. A neurostimulation device according to claim 1, wherein said plurality of electrodes are at least ten electrodes such that said multichannel electrical signals are at least ten channels of electrical signals.

3. A neurostimulation device according to claim 2, wherein said multichannel statistics includes statistics for at least all pairs of said multichannel electrical signals.

4. A neurostimulation device according to claim 1, wherein said multichannel seizure detection unit is configured to model said multichannel electrical signals based on a brain network model.

5. A neurostimulation device according to claim 4, wherein said brain network model models time-dependent variations of said multichannel statistics.

6. A neurostimulation device according to claim 4, wherein said brain network model is a Hidden Markov Model.

7. A neurostimulation device according to claim 1, wherein said multichannel seizure detection unit is configured to detect said presence of said seizure based on a time-dependent threshold.

8. A neurostimulation device according to claim 1, wherein said cost function is further dependent on a probability of a false positive detection.

9. A neurostimulation device according to claim 1, wherein said neurostimulation unit is triggered by said multichannel seizure detection unit to provide an electrical stimulation.

10. A neurostimulation device according to claim 1, wherein said neurostimulation unit is triggered by said multichannel seizure detection unit to provide a chemical stimulation.

11. A neurostimulation device according to claim 1, wherein said neurostimulation unit is triggered by said multichannel seizure detection unit to provide at least one of a visual or auditory warning.

12. A neurostimulation device according to claim 1, wherein said neurostimulation device is an implantable device.

13. A multichannel seizure detection system, comprising:
a signal interface adapted to receive multichannel electrical signals from a brain of a subject; and
a data processor configured to receive said multichannel electrical signals and detect a presence of a seizure based on multichannel statistics from said multichannel electrical signals including higher order combinations than two-channel combinations,
wherein said multichannel electrical signals are at least three channels of electrical signals,
wherein said data processor is configured to detect said presence of said seizure based on optimizing a cost function, and
wherein said cost function is dependent on a time delay between an actual seizure and a prediction of said seizure.

14. A multichannel seizure detection system according to claim 13, wherein said multichannel electrical signals are at least ten channels of electrical signals.

15. A multichannel seizure detection system according to claim 14, wherein said multichannel statistics includes statistics for at least all pairs of said multichannel electrical signals.

16. A multichannel seizure detection system according to claim 13, wherein said data processor is further configured to model said multichannel electrical signals based on a brain network model.

17. A multichannel seizure detection system according to claim 16, wherein said brain network model models time-dependent variations of said multichannel statistics.

18. A multichannel seizure detection system according to claim 16, wherein said brain network model is a Hidden Markov Model.

19. A multichannel seizure detection system according to claim 16, wherein said brain network model is a two-state model.

20. A multichannel seizure detection system according to claim 16, wherein said brain network model is a multi-state model.

21. A multichannel seizure detection system according to claim 13, wherein said data processor is configured to detect said presence of said seizure based on a time-dependent threshold.

22. A multichannel seizure detection system according to claim 13, wherein said cost function is further dependent on a probability of a false positive detection.

* * * * *